(12) United States Patent
Hanlon et al.

(10) Patent No.: US 8,257,287 B2
(45) Date of Patent: Sep. 4, 2012

(54) SAFETY CONNECTOR ASSEMBLY

(75) Inventors: James G. Hanlon, Manchester, MO (US); David Rork Swisher, St. Charles, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 1165 days.

(21) Appl. No.: 12/052,282

(22) Filed: Mar. 20, 2008

(65) Prior Publication Data
US 2009/0240178 A1 Sep. 24, 2009

(51) Int. Cl.
*A61H 7/00* (2006.01)
(52) U.S. Cl. ........................ 601/151; 601/152
(58) Field of Classification Search .......... 601/151–153; 604/4–6, 122, 537, 905
See application file for complete search history.

(56) References Cited

U.S. PATENT DOCUMENTS

| | | |
|---|---|---|
| 2,280,485 A | 4/1942 | Harris |
| 2,694,393 A | 11/1954 | Simpson |
| 2,694,395 A | 11/1954 | Brown |
| 2,893,395 A | 7/1959 | Buck |
| 3,057,001 A | 10/1962 | Rapata |
| 3,097,866 A | 7/1963 | Iversen |
| 3,287,031 A | 11/1966 | Simmons et al. |
| 3,454,006 A | 7/1969 | Langdon |
| 3,625,212 A | 12/1971 | Rosenberg et al. |
| 3,728,875 A | 4/1973 | Hartigan et al. |
| 3,733,577 A | 5/1973 | Hammond |
| 3,834,388 A | 9/1974 | Sauer |
| 4,013,069 A | 3/1977 | Hasty |
| 4,029,087 A | 6/1977 | Dye et al. |
| 4,030,488 A | 6/1977 | Hasty |
| 4,066,084 A | 1/1978 | Tillander |
| 4,091,804 A | 5/1978 | Hasty |
| 4,149,529 A | 4/1979 | Copeland et al. |
| 4,150,673 A | 4/1979 | Watt |
| 4,156,425 A | 5/1979 | Arkans |
| 4,198,961 A | 4/1980 | Arkans |
| 4,207,875 A | 6/1980 | Arkans |
| 4,207,876 A | 6/1980 | Annis |
| 4,211,439 A | 7/1980 | Moldestad |
| 4,253,449 A | 3/1981 | Arkans et al. |
| 4,280,485 A | 7/1981 | Arkans |
| 4,280,723 A | 7/1981 | Moldestad |
| 4,369,781 A | 1/1983 | Gilson et al. |
| 4,580,816 A | 4/1986 | Campbell et al. |

(Continued)

FOREIGN PATENT DOCUMENTS

BE 893623 A1 10/1982

(Continued)

OTHER PUBLICATIONS

The Kendall Company, "The New SCD Compression Sleeve", Aug. 1993, pp. 1-2, United States.
The Kendall Company, "Vascular Therapy Products Catalog", Jan. 1996, pp. 7-5 to 7-6, United States.
Tyco Healthcare Kendall, "Prevention Gets Personal", Mar. 2001, pp. 1-4, United States.

(Continued)

*Primary Examiner* — Michael A. Brown
(74) *Attorney, Agent, or Firm* — Thomas M. Johnston, Esq.

(57) ABSTRACT

A connector assembly includes first and second mating connectors that can be joined to make a fluid connection. The connectors are constructed to discriminate improper connectors so that no fluid tight connection can be formed with improper connectors. The connector assembly can be used with a system for compression therapy to prevent deep vein thrombosis.

14 Claims, 44 Drawing Sheets

U.S. PATENT DOCUMENTS

| | | | |
|---|---|---|---|
| 4,619,640 A | 10/1986 | Potolsky et al. | |
| 4,762,504 A | 8/1988 | Michaels et al. | |
| 4,790,567 A | 12/1988 | Kawano et al. | |
| 4,795,429 A | 1/1989 | Feldstein | |
| 4,804,208 A | 2/1989 | Dye | |
| D300,177 S | 3/1989 | Bellotti et al. | |
| 4,824,145 A | 4/1989 | Carlsson | |
| RE32,939 E | 6/1989 | Gardner et al. | |
| 4,867,699 A | 9/1989 | Oda et al. | |
| 4,872,736 A | 10/1989 | Myers et al. | |
| 4,887,849 A | 12/1989 | Briet | |
| 4,988,062 A | 1/1991 | London | |
| 5,007,411 A | 4/1991 | Dye | |
| 5,009,252 A | 4/1991 | Faughn | |
| 5,022,387 A | 6/1991 | Hasty | |
| 5,031,604 A | 7/1991 | Dye | |
| 5,041,025 A | 8/1991 | Haitmanek | |
| 5,062,550 A | 11/1991 | Singh | |
| 5,117,812 A | 6/1992 | McWhorter | |
| 5,123,677 A | 6/1992 | Kreczko et al. | |
| 5,156,603 A | 10/1992 | Olsen | |
| 5,165,728 A | 11/1992 | Mayer | |
| 5,176,406 A | 1/1993 | Straghan | |
| 5,186,163 A | 2/1993 | Dye | |
| 5,190,534 A | 3/1993 | Kendell | |
| 5,215,538 A | 6/1993 | Larkin | |
| 5,217,384 A | 6/1993 | Merten et al. | |
| 5,219,185 A | 6/1993 | Oddenino | |
| 5,224,932 A | 7/1993 | Lappas | |
| 5,240,289 A | 8/1993 | Gottling et al. | |
| 5,249,830 A | 10/1993 | Calmettes et al. | |
| 5,263,945 A | 11/1993 | Byrnes et al. | |
| 5,273,254 A | 12/1993 | McNaughton et al. | |
| 5,285,776 A | 2/1994 | Bertram | |
| 5,330,366 A | 7/1994 | Tsuji et al. | |
| 5,354,260 A | 10/1994 | Cook | |
| 5,370,423 A | 12/1994 | Guest | |
| 5,383,894 A | 1/1995 | Dye | |
| 5,387,110 A | 2/1995 | Kantner et al. | |
| D357,736 S | 4/1995 | Dye | |
| 5,435,009 A | 7/1995 | Schild et al. | |
| 5,437,610 A | 8/1995 | Cariapa et al. | |
| 5,443,289 A | 8/1995 | Guest | |
| D363,988 S | 11/1995 | Dye | |
| 5,478,119 A | 12/1995 | Dye | |
| 5,507,732 A | 4/1996 | McClure et al. | |
| 5,509,911 A | 4/1996 | Cottone, Sr. et al. | |
| 5,518,416 A | 5/1996 | Kantner et al. | |
| 5,546,934 A | 8/1996 | Kaigler et al. | |
| D375,357 S | 11/1996 | Silver | |
| 5,575,762 A | 11/1996 | Peeler et al. | |
| 5,588,954 A | 12/1996 | Ribando et al. | |
| 5,588,955 A | 12/1996 | Johnson, Jr. et al. | |
| 5,591,143 A | 1/1997 | Trombley, III et al. | |
| 5,591,200 A | 1/1997 | Cone et al. | |
| 5,626,556 A | 5/1997 | Tobler et al. | |
| 5,637,102 A | 6/1997 | Tolkoff et al. | |
| 5,695,224 A | 12/1997 | Grenier | |
| 5,711,757 A | 1/1998 | Bryant | |
| 5,725,425 A | 3/1998 | Rump et al. | |
| 5,725,485 A | 3/1998 | Ribando et al. | |
| 5,725,511 A | 3/1998 | Urrutia | |
| 5,735,841 A | 4/1998 | Bourguignon et al. | |
| 5,743,755 A | 4/1998 | Aoki | |
| 5,782,808 A | 7/1998 | Folden | |
| 5,810,398 A * | 9/1998 | Matkovich | 285/3 |
| 5,843,007 A | 12/1998 | McEwen et al. | |
| 5,876,359 A | 3/1999 | Bock et al. | |
| 5,897,142 A | 4/1999 | Kulevsky | |
| 5,947,937 A | 9/1999 | Urrutia et al. | |
| 5,951,502 A | 9/1999 | Peeler et al. | |
| 5,971,927 A | 10/1999 | Mine | |
| 5,971,972 A | 10/1999 | Rosenbaum | |
| 5,988,704 A | 11/1999 | Ryhman | |
| 5,989,204 A | 11/1999 | Lina | |
| 5,989,240 A | 11/1999 | Strowe | |
| 6,062,244 A | 5/2000 | Arkans | |
| 6,113,572 A | 9/2000 | Gailey et al. | |
| 6,126,610 A | 10/2000 | Rich et al. | |
| 6,129,688 A | 10/2000 | Arkans | |
| 6,145,539 A | 11/2000 | Wilcox et al. | |
| 6,152,495 A | 11/2000 | Hoffmann et al. | |
| 6,156,025 A | 12/2000 | Niedospial, Jr. | |
| 6,165,149 A * | 12/2000 | Utterberg et al. | 604/5.01 |
| 6,193,697 B1 | 2/2001 | Jepson et al. | |
| 6,231,532 B1 | 5/2001 | Watson et al. | |
| 6,238,230 B1 | 5/2001 | Sadler et al. | |
| 6,257,626 B1 | 7/2001 | Campau | |
| 6,257,627 B1 | 7/2001 | Fujiwara et al. | |
| 6,296,617 B1 | 10/2001 | Peeler et al. | |
| D450,838 S | 11/2001 | Cise et al. | |
| 6,319,215 B1 | 11/2001 | Manor et al. | |
| 6,402,207 B1 | 6/2002 | Segal et al. | |
| 6,423,053 B1 | 7/2002 | Lee | |
| 6,436,064 B1 | 8/2002 | Kloecker | |
| 6,440,093 B1 | 8/2002 | McEwen et al. | |
| 6,468,237 B1 | 10/2002 | Lina | |
| 6,523,861 B1 | 2/2003 | Clancy et al. | |
| 6,537,099 B2 | 3/2003 | Herlinger et al. | |
| 6,544,202 B2 | 4/2003 | McEwen et al. | |
| 6,547,284 B2 | 4/2003 | Rose et al. | |
| 6,581,906 B2 | 6/2003 | Pott et al. | |
| 6,592,534 B1 | 7/2003 | Rutt et al. | |
| 6,612,624 B1 | 9/2003 | Segal et al. | |
| 6,620,119 B1 | 9/2003 | Utterberg et al. | |
| 6,629,941 B1 | 10/2003 | Ishibashi et al. | |
| 6,652,509 B1 | 11/2003 | Helgren et al. | |
| 6,666,839 B2 | 12/2003 | Utterberg et al. | |
| 6,802,836 B2 | 10/2004 | Bouphavichith et al. | |
| 6,802,855 B2 | 10/2004 | Ellingboe et al. | |
| 6,827,728 B2 | 12/2004 | Ellingboe et al. | |
| 6,949,084 B2 | 9/2005 | Marggi et al. | |
| 7,007,983 B2 | 3/2006 | Arosio | |
| 7,137,654 B2 | 11/2006 | Segal et al. | |
| 7,140,592 B2 | 11/2006 | Phillips | |
| 7,240,926 B2 | 7/2007 | Dalle et al. | |
| 7,347,853 B2 | 3/2008 | DiFiore et al. | |
| 7,484,769 B2 | 2/2009 | Domash et al. | |
| 7,490,620 B2 | 2/2009 | Tesluk et al. | |
| 7,967,766 B2 * | 6/2011 | Ravikumar | 602/13 |
| 2002/0096883 A1 | 7/2002 | Youssefifar | |
| 2003/0001387 A1 | 1/2003 | Tawara et al. | |
| 2003/0045153 A1 | 3/2003 | Yamawaki | |
| 2003/0075923 A1 | 4/2003 | Lepoutre | |
| 2003/0144647 A1 | 7/2003 | Miyahara | |
| 2003/0191445 A1 | 10/2003 | Wallen et al. | |
| 2003/0191453 A1 * | 10/2003 | Velez et al. | 604/537 |
| 2004/0030373 A1 | 2/2004 | Ellingboe et al. | |
| 2004/0034324 A1 | 2/2004 | Seese et al. | |
| 2004/0039317 A1 | 2/2004 | Souney et al. | |
| 2004/0111078 A1 | 6/2004 | Miyahara | |
| 2004/0201216 A1 | 10/2004 | Segal et al. | |
| 2004/0227120 A1 | 11/2004 | Raybuck | |
| 2005/0043781 A1 * | 2/2005 | Foley | 623/1.15 |
| 2005/0085794 A1 | 4/2005 | Denoth et al. | |
| 2005/0090805 A1 | 4/2005 | Shaw et al. | |
| 2005/0143682 A1 | 6/2005 | Cook et al. | |
| 2005/0234407 A1 | 10/2005 | Spohn et al. | |
| 2006/0004245 A1 | 1/2006 | Pickett et al. | |
| 2006/0025751 A1 | 2/2006 | Roy et al. | |
| 2006/0116660 A1 | 6/2006 | Cawley | |
| 2006/0189961 A1 | 8/2006 | Miyahara | |
| 2007/0020752 A1 * | 1/2007 | Russell et al. | 435/297.5 |
| 2007/0060898 A1 | 3/2007 | Shaughnessy et al. | |
| 2007/0073270 A1 | 3/2007 | Christensen et al. | |
| 2007/0088327 A1 | 4/2007 | Guala | |
| 2008/0077063 A1 | 3/2008 | Meyer et al. | |
| 2008/0077176 A1 | 3/2008 | Hanlon et al. | |
| 2008/0228125 A1 | 9/2008 | Brugger et al. | |
| 2008/0300542 A1 | 12/2008 | Kitani et al. | |

FOREIGN PATENT DOCUMENTS

| | | |
|---|---|---|
| DE | 2907832 A1 | 9/1980 |
| DE | 20301094 U1 | 4/2003 |
| DE | 10333118 B4 | 2/2008 |
| EP | 0151519 A1 | 8/1985 |
| EP | 0585633 A1 | 3/1994 |

| | | | |
|---|---|---|---|
| EP | 0634190 | A2 | 1/1995 |
| EP | 0832666 | A2 | 4/1998 |
| EP | 0880978 | A2 | 12/1998 |
| FR | 1171861 | A | 1/1959 |
| FR | 2863162 | A1 | 6/2005 |
| GB | 2343723 | | 5/2000 |
| WO | 8100053 | A1 | 1/1981 |
| WO | 9012606 | A2 | 11/1990 |
| WO | 9822175 | A1 | 5/1998 |
| WO | 0123026 | A1 | 4/2001 |
| WO | 2004073778 | A1 | 9/2004 |

OTHER PUBLICATIONS

Tyco Healthcare Kendall, "SCD Response Sequential Compression System Catalog", Mar. 2000, pp. 1-2, United States.

Tyco Healthcare Kendall, "SCD Soft Sleeve Catalog", Apr. 2001, pp. 1-2, United States.

Kendall SCD, "Sequential Compression Sleeves," Jan. 1993, pp. 1-6, United States.

* cited by examiner

SAFETY CONNECTOR ASSEMBLY

TECHNICAL FIELD

The present disclosure relates to safety connectors for use in medical applications, particularly for use with compression therapy devices. The present disclosure also relates to discriminating safety connector assemblies and, more particularly, to a discriminating safety connector assembly for fluidly coupling at least two lumens capable of forming a non-leaking fluid circuit.

BACKGROUND OF THE INVENTION

In a medical environment, many devices have tubing adapted for manual connection in order to provide a fluid connection between devices or between a device and a patient including enteral feeding pumps and intravenous feeding lines. Each of these devices includes one or more connectors that a user or practitioner may inadvertently connect together. This may result in the successful connection of incompatible devices or the supply of fluid or nutrient to an improper intravenous line or a device such as an inflatable bladder used in deep vein thrombosis therapy. Successful connection of incompatible devices may harm patients or damage equipment.

When connecting a medical device to a fluid supply, a non-leaking seal must be made between compatible devices and/or fluid sources. Thus, connections must be designed to provide an adequate seal between sealing surfaces when the devices and/or supply are compatible. Typical devices have a male and female connector that, when pressed together, form a fluid tight seal. The connectors come in different sizes and shapes and typically have O-rings or gaskets to help create a fluid tight seal.

Examples of a medical device connected to a fluid supply include compression therapy devices that are wrapped around a limb to prevent peripheral edema and conditions that form blood clots such as deep vein thrombosis. These devices typically include at least one air bladder that is sized and shaped for being applied around the limb. The bladder is inflated and deflated to artificially stimulate blood flow throughout the appendage that would normally result from, for example, walking. An example of such a device that is configured for disposal about a foot is shown in U.S. Pub. No. 2005/0187499. Typically, these compression devices are connected to a tube set which provides fluid communication from a pressure source to the compression device. A controller is employed to regulate the flow of fluid from the pressure source to the compression device.

The compression device, tube set and controller each contain connections for connecting and disconnecting the compression device from the pressure source. It is desirable to avoid erroneous connection of a medical device other than the compression device, for example an intravenous needle, to the pressure source.

SUMMARY OF THE INVENTION

In one aspect of the present invention, a connector assembly for use in making discriminating fluid connection between a source of fluid and a fluid receiving object, the connector assembly generally comprises a first connector having a coupling portion. The coupling portion includes a sealing surface and a non-sealing surface, the non-sealing surface being located closer to a free end of the first connector than the sealing surface and having a larger diameter than the sealing surface. A second connector comprises a conduit having an open outer end and being sized to mate with the coupling portion. The conduit has at least one of a hardness and a wall thickness selected so that the conduit deforms into fluid-tight engagement with the sealing surface of the first connector while remaining in engagement with the non-sealing surface.

In another aspect, a compliant connector is used in making a discriminating connection with another connector having a non-sealing surface and a sealing surface where the non-sealing surface is located closer to a free end of the other connector and has a larger diameter than the sealing surface. The compliant connector generally comprises a conduit having a hardness and wall thickness selected for simultaneously engaging the non-sealing surface and the sealing surface while deforming into fluid-tight engagement with the sealing surface.

In a further aspect, a method of making a discriminating connection for medical uses generally comprises providing a first connector having a coupling portion. The coupling portion includes a sealing surface and a non-sealing surface, the non-sealing surface being located closer to a free end of the first connector than the sealing surface and having a larger diameter than the sealing surface. A second connector comprising a conduit having an open outer end, the conduit being sized to mate with the coupling portion is provided. The first connector and the second connector are mated so that the conduit slides over the non-sealing surface of the second connector and past the non-sealing surface to the non-sealing surface of the first connector. The conduit has at least one of a hardness and a wall thickness selected so that the conduit deforms into fluid-tight engagement with the sealing surface of the first connector while remaining in engagement with the non-sealing surface.

Other objects and features will be in part apparent and in part pointed out hereinafter.

BRIEF DESCRIPTION OF THE DRAWINGS

Embodiments of the present disclosure are described herein below with reference to the drawings wherein.

Corresponding reference characters indicate corresponding parts throughout the drawings.

DESCRIPTION OF THE PREFERRED EMBODIMENTS

Figure 1:
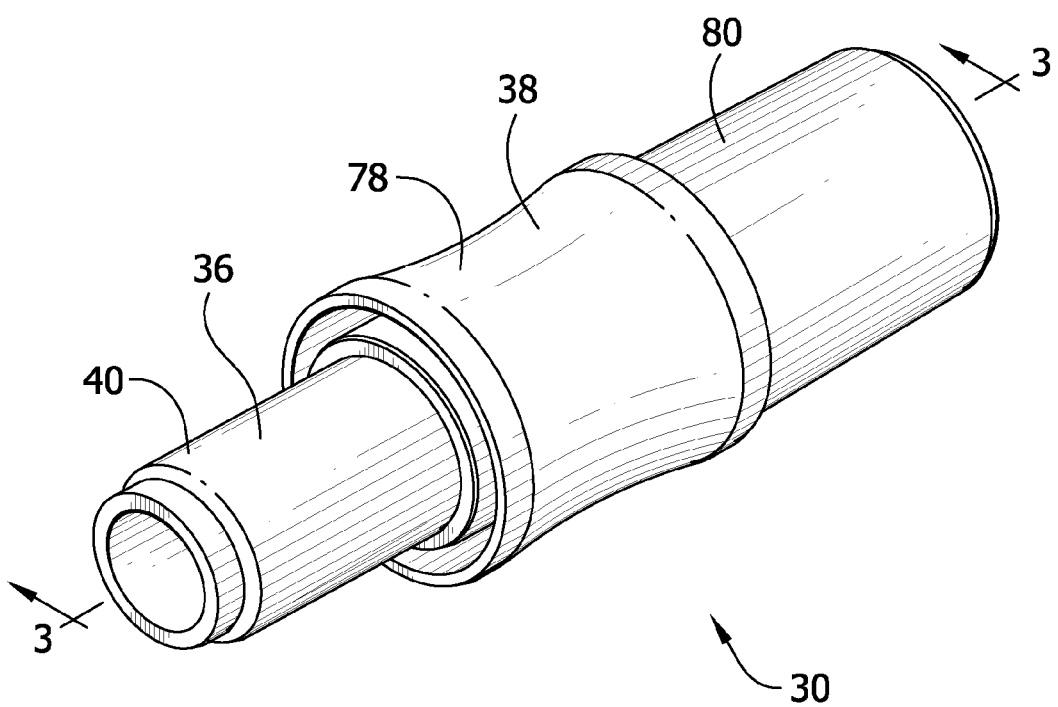
FIG. 1 is a perspective of a connector assembly with a first and second connector of the connector assembly engaged.
Figure 2:
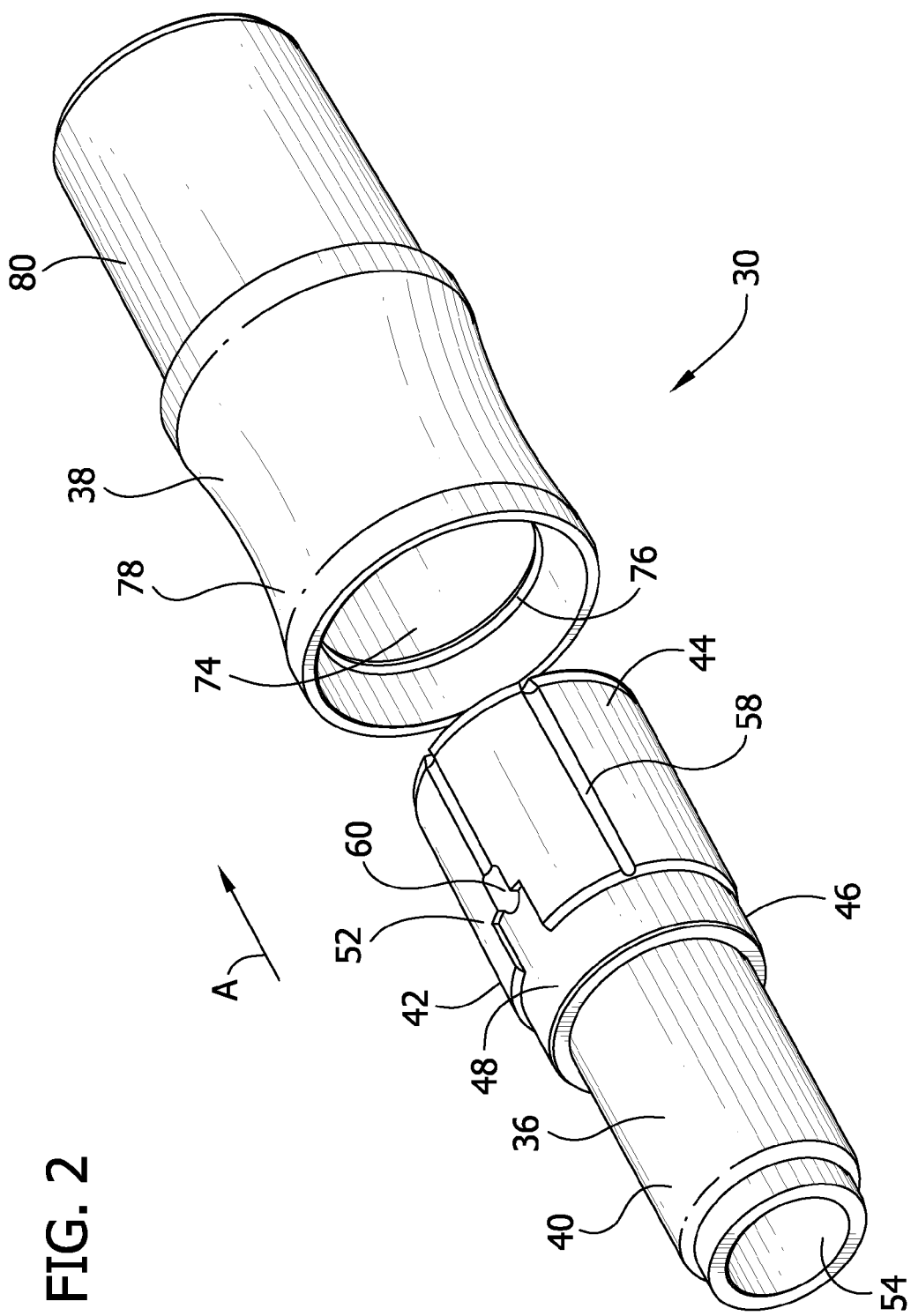
FIG. 2 is a perspective of the connector assembly with the first and second connector separated.
Figure 40:
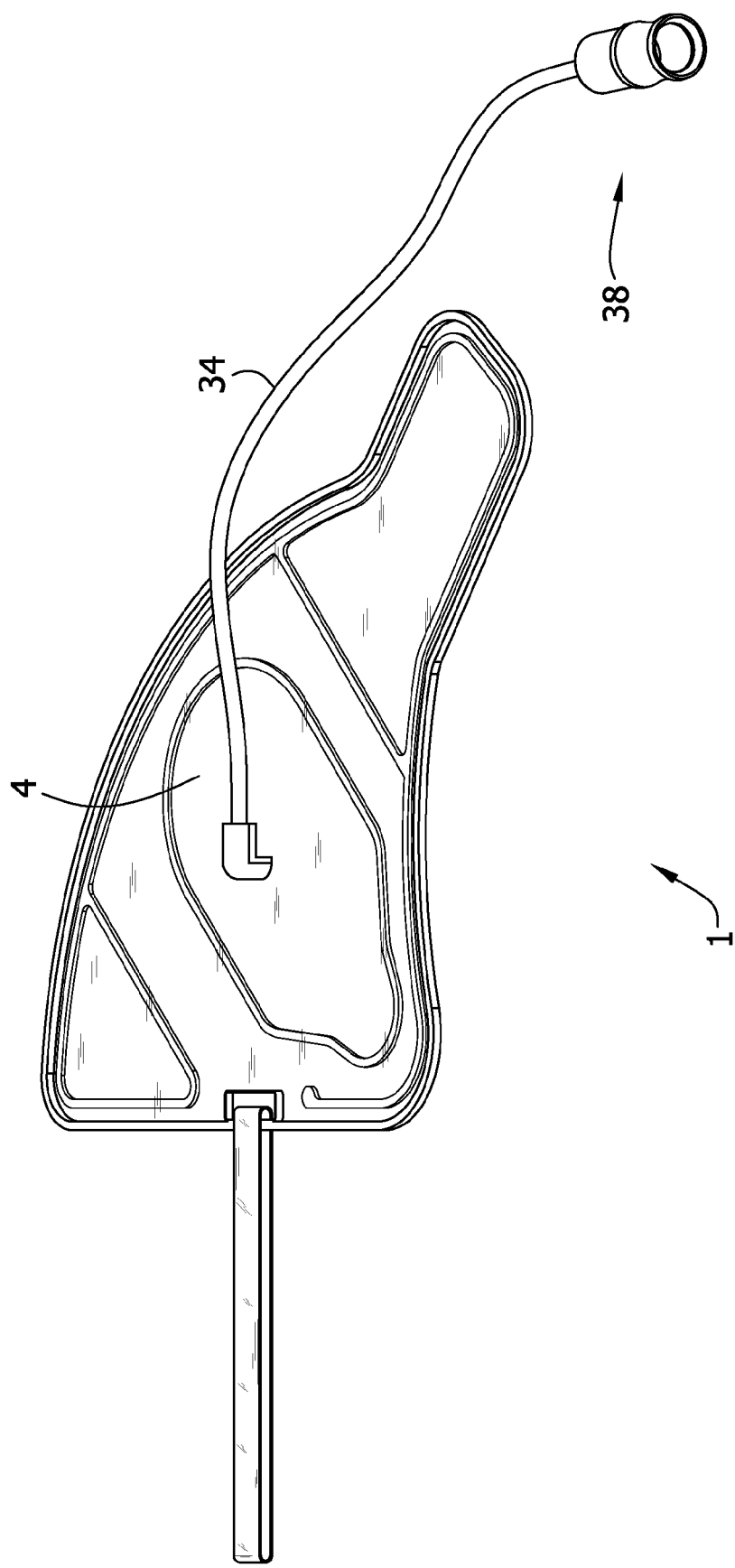
FIG. 40 is a perspective of a compression therapy device showing an inflatable bladder and an enlarged view of the connector.

Referring now to the drawings, a connector assembly 30 constructed according to the principles of the present invention is shown in FIGS. 1 and 2 to comprise a first connector 36 and a second connector 38. As described more fully hereinafter, the first and second connectors 36, 38 are capable of discriminating connection to preferentially achieve fluid-tight connection of the connectors, and avoid fluid-tight connection with non-complying connectors. The connector system 30 may be used, for example, to connect a controller 2 to a compression therapy device 1 for cyclically supplying air pressure to a bladder 4 of the device (see, FIGS. 40 and 41). The compression therapy device 1 illustrated in FIG. 40 is of the type which is applied to the foot for repeatedly compressing the foot to force blood out of the foot and discourage pooling of blood in the foot that can lead to clots. Although a foot compression therapy device 1 is illustrated, other types of compression therapy devices can be employed, such as those that are applied to the leg. Other examples of foot and leg devices are disclosed in U.S. Pat. Nos. 5,626,556 and 5,795,312. Moreover, the connector assembly 30 can be used for other types of medical fluid connections such as the connection of an enteral feeding bag to a patient.

Figure 41:
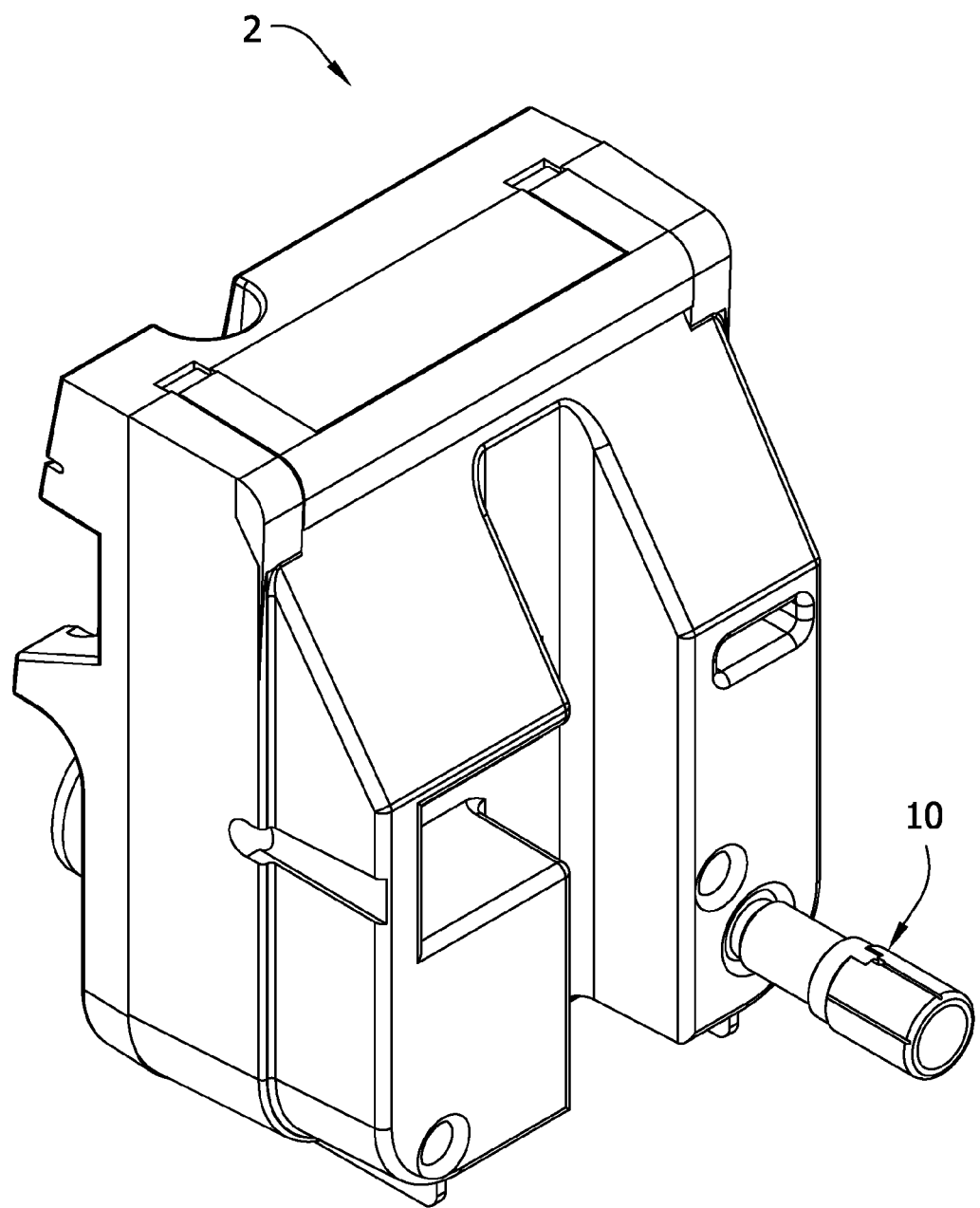
FIG. 41 is a perspective of a compression therapy device controller with an enlarged view of the connector.
Figure 42:
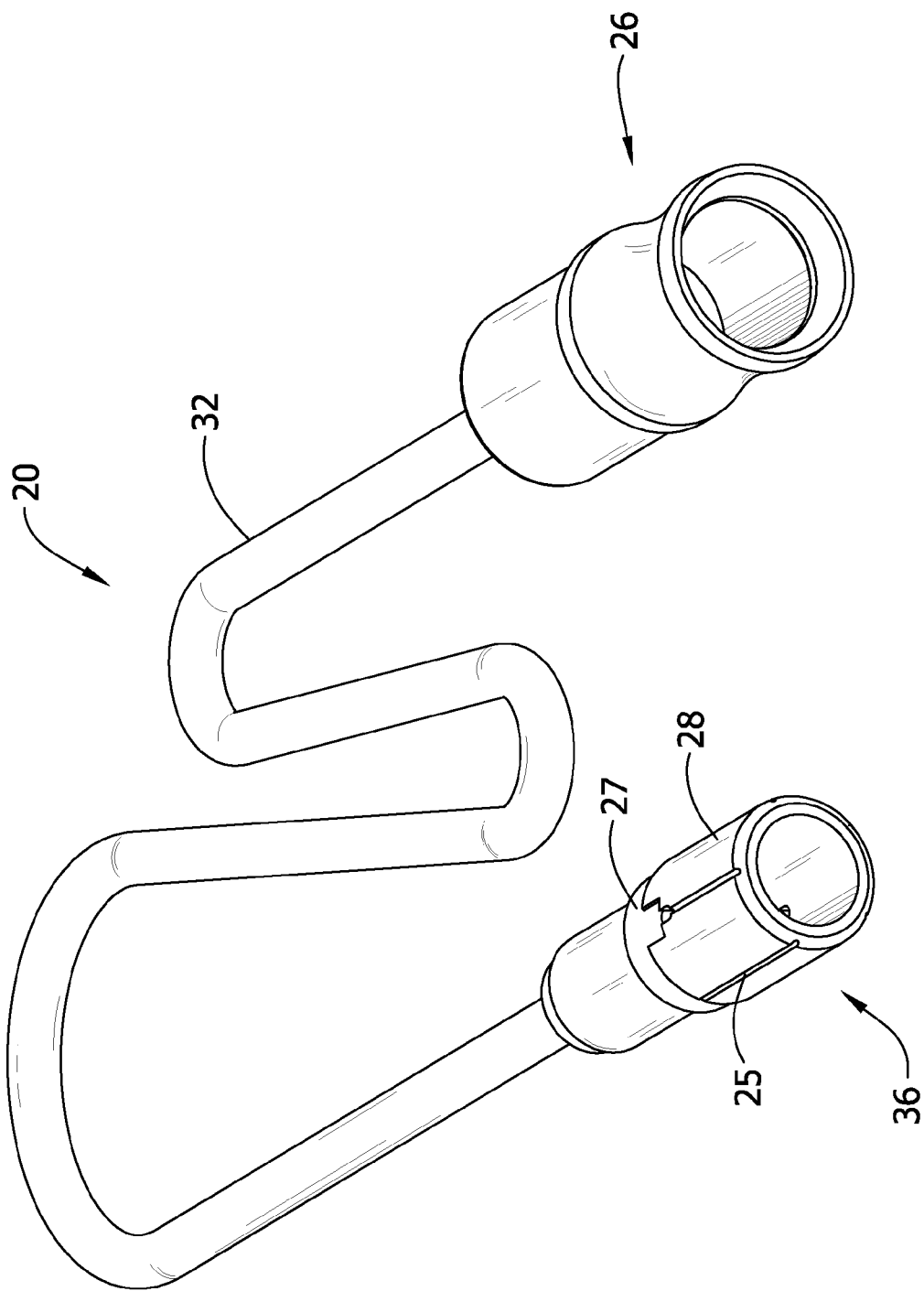
FIG. 42 is an enlarged perspective of a tube set.

In the illustrated example, a tube set 20 (FIG. 42) is used to selectively interconnect the compression therapy device 1 and the controller 2. The first connector 36 is attached to a first tubing 32 of the tube set 20, and the second connector 38 is attached to a second tubing 34 extending from the bladder 4 of the compression therapy device 1 (FIG. 40). A third connector 10 having substantially the same construction as the first connector 36 is attached to the controller 2 (FIG. 41), and a fourth connector 26 having substantially the same construction as the second connector 38 is attached to the opposite end of the tubing 32 of the tube set 20 (FIG. 42). In order to make fluid connection for delivering of pressurized air from the controller 2 to the compression therapy device 1, the fourth connector 26 of the tube set 20 is engaged with the third connector 10 of the controller, and the first connector 36 of the tube set is engaged with the second connector 38 of the compression therapy device. Because of the structural identity of the first connector 36 and third connector 10, and of the second connector 38 and the fourth connector 26, only the first and second connectors will be described in detail hereinafter.

Referring to FIGS. 1-6, the first connector 36 has an attachment portion 40 that accepts the tubing 32. However, the attachment portion 40 could be directly connected to an object other than tubing, such as the third connector 10 is directly connected to the controller 2 (FIG. 41). The second connector 38 has an attachment portion 80 and a receptacle 78. The receptacle 78 has a roughly hourglass shape, so the user can grasp and hold the connector assembly 30 and to aid the user in engaging the second connector 38 to the first connector 36, as shown in FIG. 1.

Referring to FIG. 2, a coupling portion 42 of the first connector 36 has a first end 44 and a second end 46. The second end 46 is suitably attached to the attachment portion 40, such as by solvent bending or RF welding, or may be formed as one piece of material with the attachment portion. The attachment portion 40 is sealingly received in the tubing 32 of the tube set 20 (FIG. 42). The coupling portion 42 includes a sealing surface 48 and a non-sealing surface 52. The sealing surface 48 extends around the perimeter of the coupling portion 42 at the second end 46. The shape and contour of the coupling portion 42 is not restricted to that of the illustrated embodiment, so long as the coupling portion can engage and form a seal with the second connector 38, as will be described. The non-sealing surface 52 has a greater diameter than the sealing surface 48. A number of circumferentially spaced channels 58 in the non-sealing surface 52 extend lengthwise of the first connection 36. Two of the channels 58 communicate with openings 60 extending radially through the first connector 36 to an inner surface 54 thereof. The channels 58 and openings 60 operate to inhibit the formation of a sealing connection.

Figure 3:
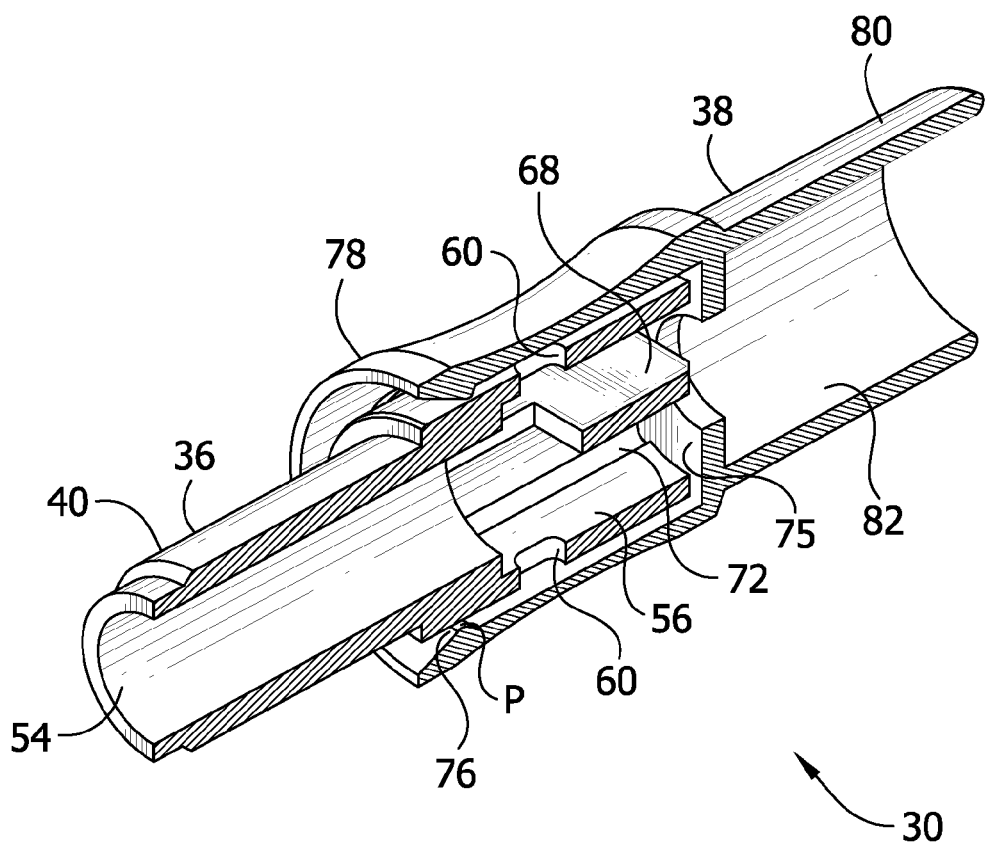
FIG. 3 is a perspective longitudinal section of the connector assembly shown in FIG. 1.

The receptacle 78 of the second connector 38 has an interior surface 74 and an annular shoulder 75 at the inner end of the interior of the receptacle (FIG. 3). The shoulder 75 defines a stop surface that limits the distance the first connector 36 can be inserted into the receptacle 78 and axially positions the first connector 36 with respect to the receptacle 78. An annular sealing flange 76 projects radially inward of the inner surface 74 of the receptacle 78 near the open end of the receptacle. As illustrated, the sealing flange 76 is formed as one piece of material with the receptacle 78. However, a sealing member (not shown) may be formed separately from the receptacle (e.g., as an O-ring) and secured to the receptacle such as by being received in a circumferential groove formed in the inner surface of the receptacle.

The user must push, in the direction of the arrow "A" in FIG. 2, the first end 44 of the first connector 36 into the receptacle 78 of the second connector 38, such that the non-sealing surface 52 passes beyond the sealing flange 76. Unless the user pushes the connectors 36, 38 together, a fluid tight seal will not form because of longitudinal channels 58 disposed about the outer surface of coupling portion 42. The sealing flange 76 cannot conform into the channels 58 that extend past the flange allowing fluid to pass the flange on the non-sealing surface 52 of the first connector 36. However, when the sealing surface 48 moves into registration with the sealing flange 76, the flange is able to sealingly conform to the sealing surface to make a fluid tight connection with the sealing surface.

The open space defined by the longitudinal channels 58 prevents flush engagement of coupling portion 42 with the surface of a non-compliant connector or fluid conduit (lumen). The longitudinal channels 58 may have widths, depths, or lengths other than illustrated herein. One or more longitudinal channels 58 may be oriented parallel, offset, or undulating with the longitudinal axis of the connector 30. The longitudinal channels 58 can be replaced with a raised surface or roughness on the non-sealing surface 52. In addition, the openings 60 defined through a wall 62 help prevent a fluid seal between the first connector 36 and a non-compliant connector. An opening 60 is not limited to size and shape provided the opening leaks with a non-compliant connector attached to the first connector 36. One or more openings 60 diametrically opposed about the wall 62 facilitate leakage with a non-compliant connector.

Figure 2A:
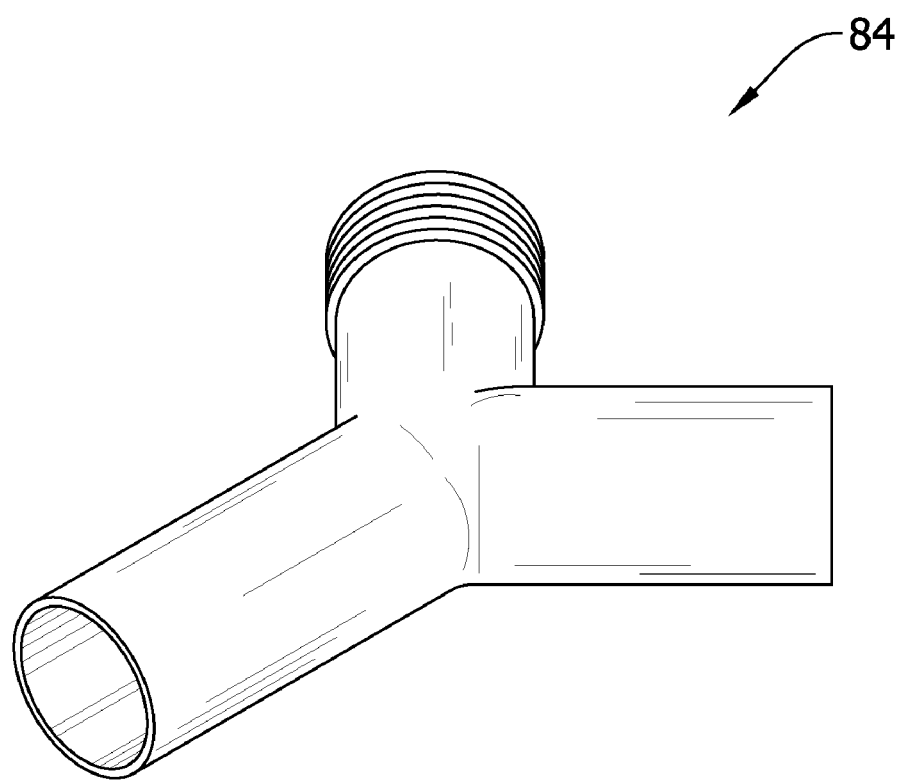
FIG. 2A is a perspective of a "Y" connector releasably attachable to the first or second connector.

An inner surface 54 of the first connector 36 and inner surface 74 of the second connector 38 form a fluid pathway therethrough. The inner surfaces (54, 74) are formed to pass fluid according to the particular flow requirements of a medical system such as the controller 2 and compression therapy device 1. Attachment portion 40 or attachment portion 80 is not restricted to one port. A "Y" connector 84 (FIG. 2A) is releasably attachable to the attachment portion (40, 80) of either connector 36, 38 to increase the number of fluids or divert pressurized air to more than one bladder, in the case of compression sleeve.

FIG. 3 illustrates the connector assembly engaged, without the tubing 32, 34 attached. In use, the first tubing 32 (not shown in FIG. 3) is sealingly attached to an inner surface 82 of the attachment portion 80. The second tubing (not shown in FIG. 3) is attached to attachment portion 40. The point contact "P" seals the connector assembly 30 upon contact between the sealing flange 76 and the sealing surface 48 of the first connector 36. The tubing 32, 34 is attached in a suitable manner such as by using solvent bonding, RF welding, or other attaching means known in the art.

Figure 4:
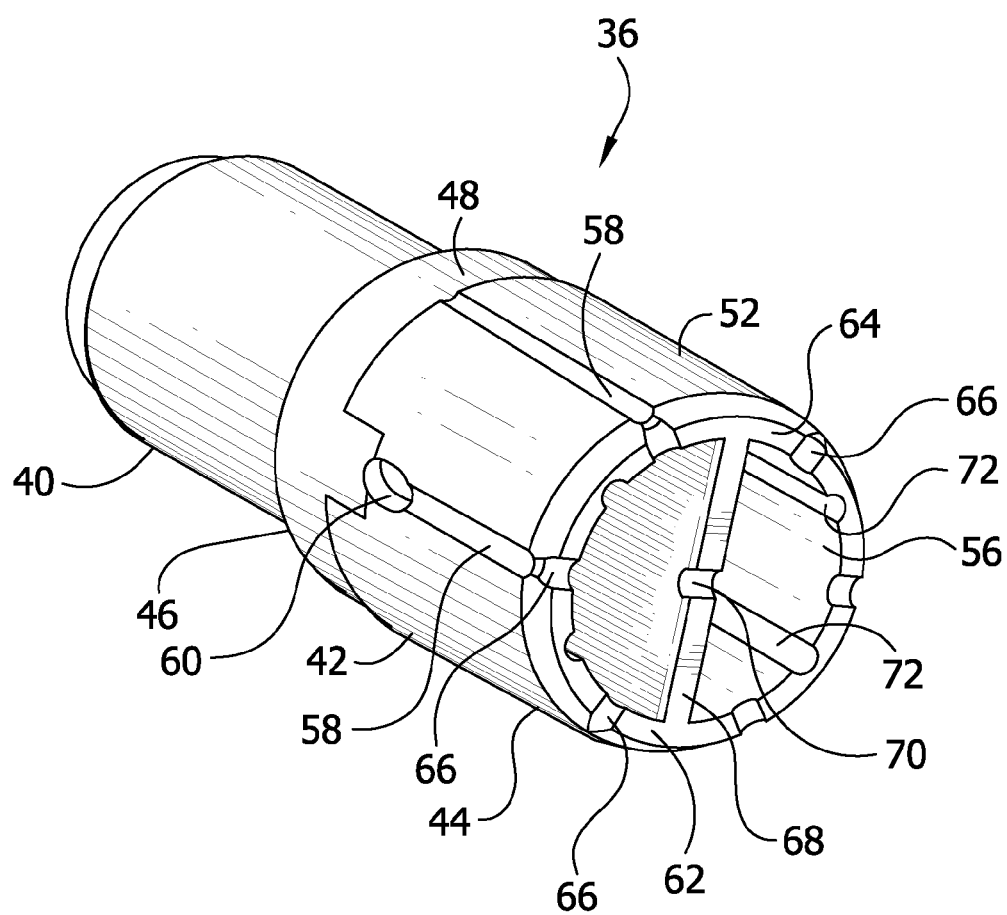
FIG. 4 is a perspective of the first connector of the connector assembly shown in FIG. 1 seen from an end and to a side.
Figure 5:
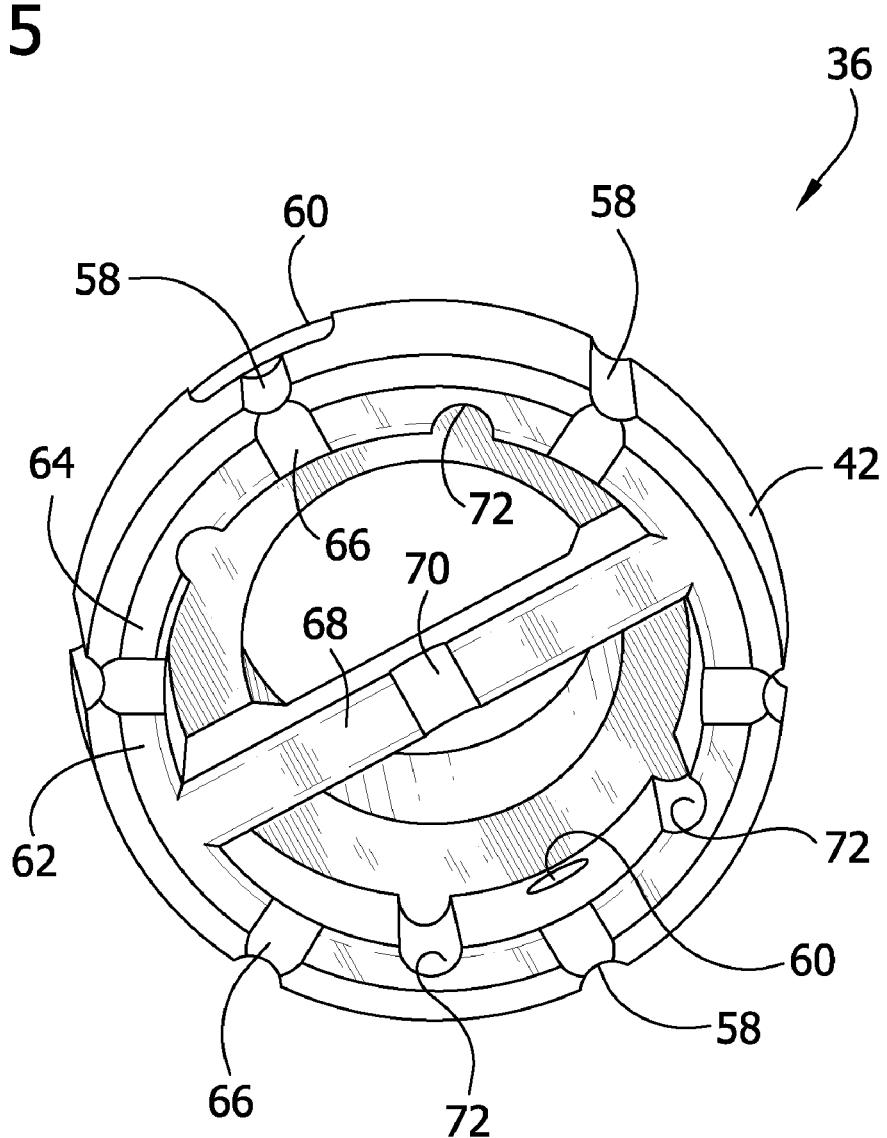
FIG. 5 is a perspective of the first connector seen substantially from the end.
Figure 6:
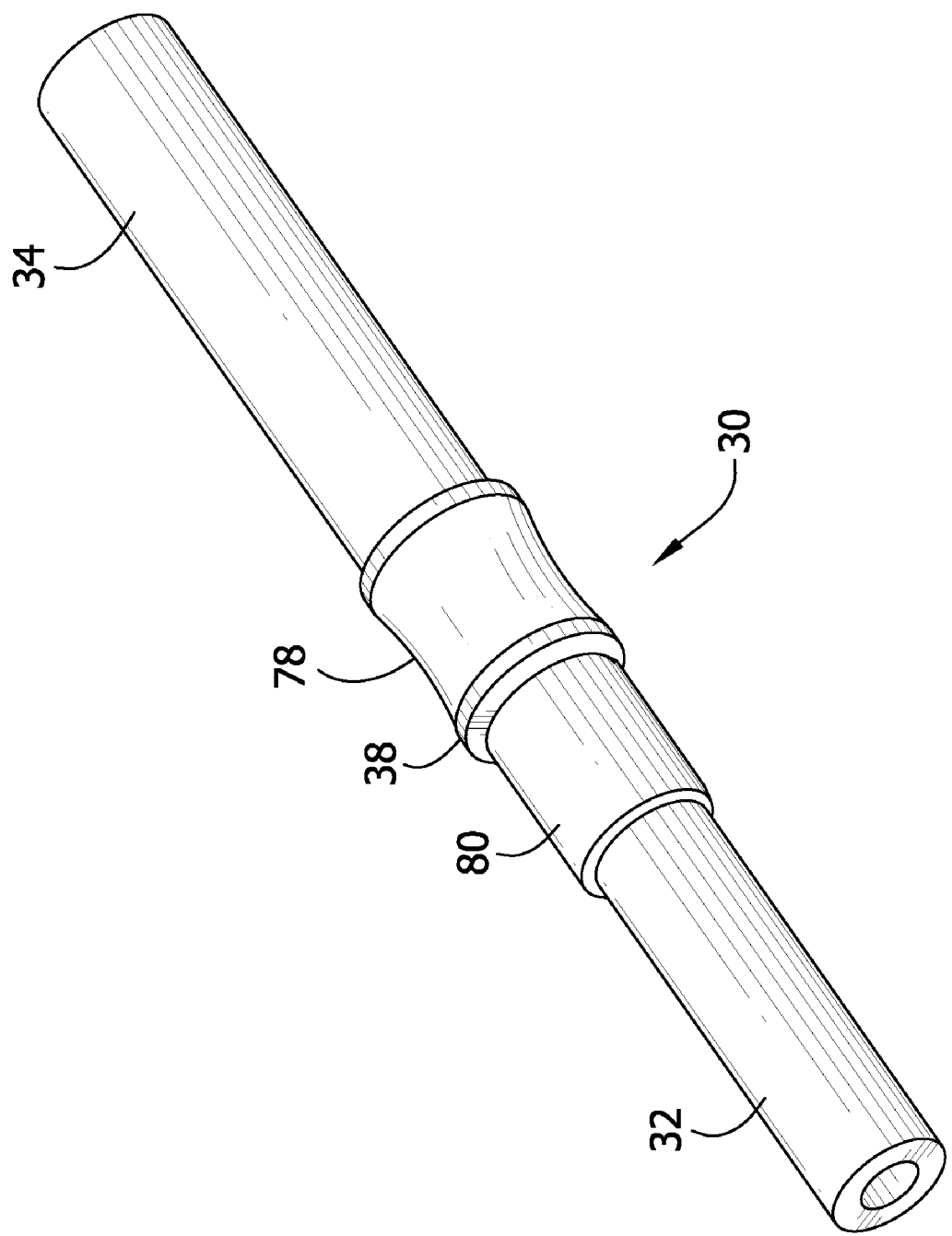
FIG. 6 is a perspective of the connector assembly shown in FIG. 1 having tubing attached.

FIGS. 4 and 5 show a transverse wall 68 at the first end 44 of the first connector 36. The transverse wall 68 has a longitudinal cavity 70 across its face. The transverse wall 68 extends along the longitudinal axis for substantially the length of the non-sealing surface 52 and inhibits the insertion of tubes or other connectors (not shown) into the first connector 36. One or more longitudinal cavities 72 extend along the inner surface 56 at the first end 44. The non-sealing surface 52 has a first face 64 with transverse cavities 66 disposed at spaced locations around the perimeter of the first face 64. Each transverse cavity 66 connects to a corresponding one of the longitudinal channels 58 formed in the wall 62 of the coupling portion 42 of first connector 36. This allows fluid to escape between the first connector 36 and a non-compliant connector. Likewise, the openings 60 allow fluid to escape when a seal is not formed with the sealing surface 48. The number and arrangement of channels 58, openings 60 and cavities 66 may be other than described without departing from the scope of the present invention.

The cavities 66 prevent a seal between the first face 64 and a surface of a non-compliant connector. Each cavity 66 aligns with its corresponding outer longitudinal channels 58 to provide a path for leakage when the first connector 36 is inserted into a non-compliant connector. The transverse wall 68 prevents inserting a non-compliant connector into the first connector 36. The cavity 70 helps prevent a sealing surface between the first face 64 and a surface of a non-complaint connector. Likewise, inner longitudinal cavities 72 and the openings 60 though the wall 62 help prevent sealing with a non-compliant connector on the inside or outside of the first connector 36. The open spaces defined by the cavities 66 prevent flush engagement with coupling portion 42 and a surface of a non-compliant connector. A cavity or channel (66, 70, 72, 58) is not limited to a specific width, depth, or length. A cavity or channel (66, 70, 72, 58) is not restricted to orientation and can be parallel, offset or undulating. The present invention is not restricted to one non-sealing surface 52 or one sealing surface 48.

Figure 7:
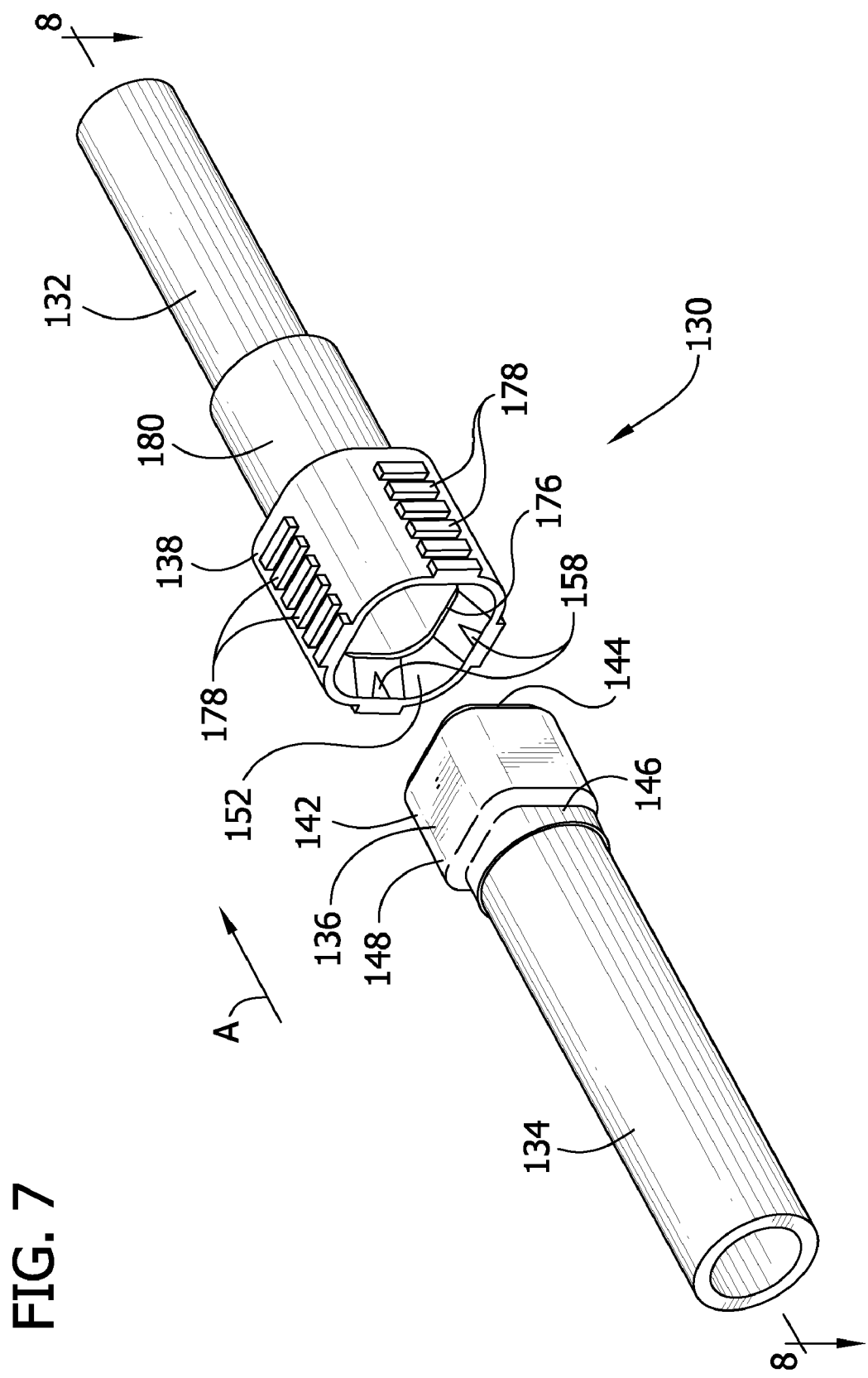
FIG. 7 is a perspective of an alternate embodiment of the connector assembly showing two separated connectors with tubing attached.
Figure 8:
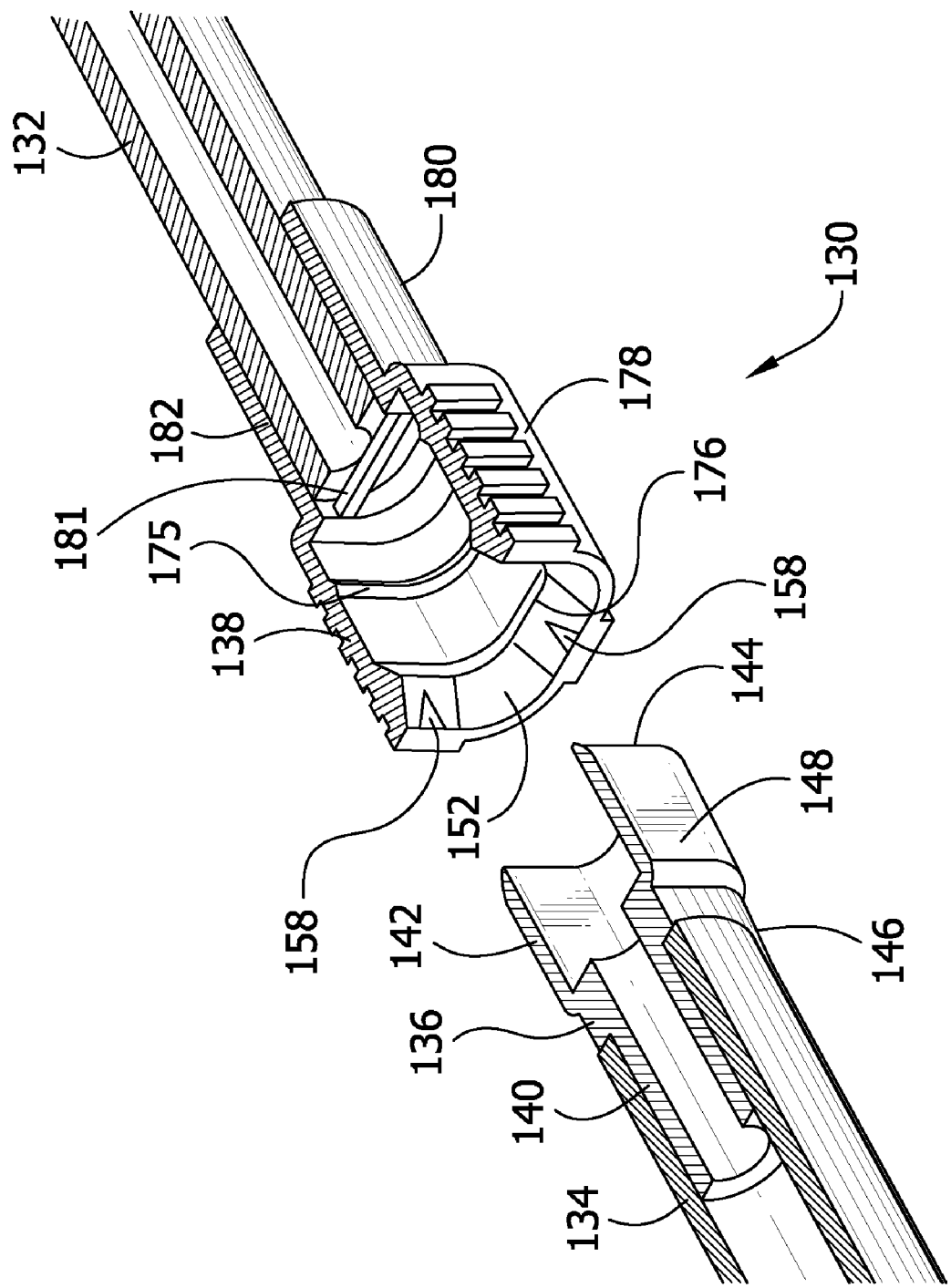
FIG. 8 is a perspective longitudinal section of the connector assembly shown in FIG. 7.

FIGS. 7 and 8 illustrate an alternative connector assembly 130. Parts of the connector assembly 130 generally corresponding to those of the connector assembly 30 will be given the same number, plus "100." A first connector 136 of the connector assembly 130 has a first end 144 and a second end 146. Located generally between the first and second ends 144, 146 is a sealing surface 148. The coupling portion 142 is rectangular with rounded corners and sized to fit into the opening of a second connector 138, in the direction of arrow "A". The second connector 138 defines a receptacle in a housing of the second connector to receive the first connector 136. An outwardly flared non-sealing surface 152 is located at the open end of the second connector 138. Triangular channels 158 in the non-sealing surface provide fluid communication paths to locations outside the connectors 136, 138 to inhibit sealing.

The user holds the second connector 138 using raised ribs 178 to grip and insert the first connector 136 into the second connector 138. In addition to functioning as grips, the ribs 178 also prevent a sealing connection between the second connector 138 and a tube or the like (not shown) received over the exterior of the second connector. The first connector 136 is inserted with its first end 144 passing beyond a sealing flange 176 located inside the second connector 138. The resilient sealing flange 176 conforms to the sealing surface 148 to form a fluid tight seal, after the sealing surface 148 passes beyond the non-sealing surface 152 and engages the flange 176. The user stops applying force when the face of the first end 144 abuts a shoulder 175 a distance beyond the sealing flange 176 of the second connector 138. A bar 181 is located at the inner end of the second connector 138 to inhibit a tube (not shown) from sealingly abutting a first tube 132 inserted inside an attachment portion 180 of the second connector.

The first tubing 132 forms a sealing interference fit with the inner surface 182 of the attachment portion 180. A second tubing 134 is inserted over an attachment portion 140 (FIG. 8), at the second end 146 of the coupling portion 142. The first and second tubings 132, 134 are attached in suitable ways to the first and second connectors 136, 138. This forms a fluid conduit as part of a medical system when properly connected.

Figure 9:
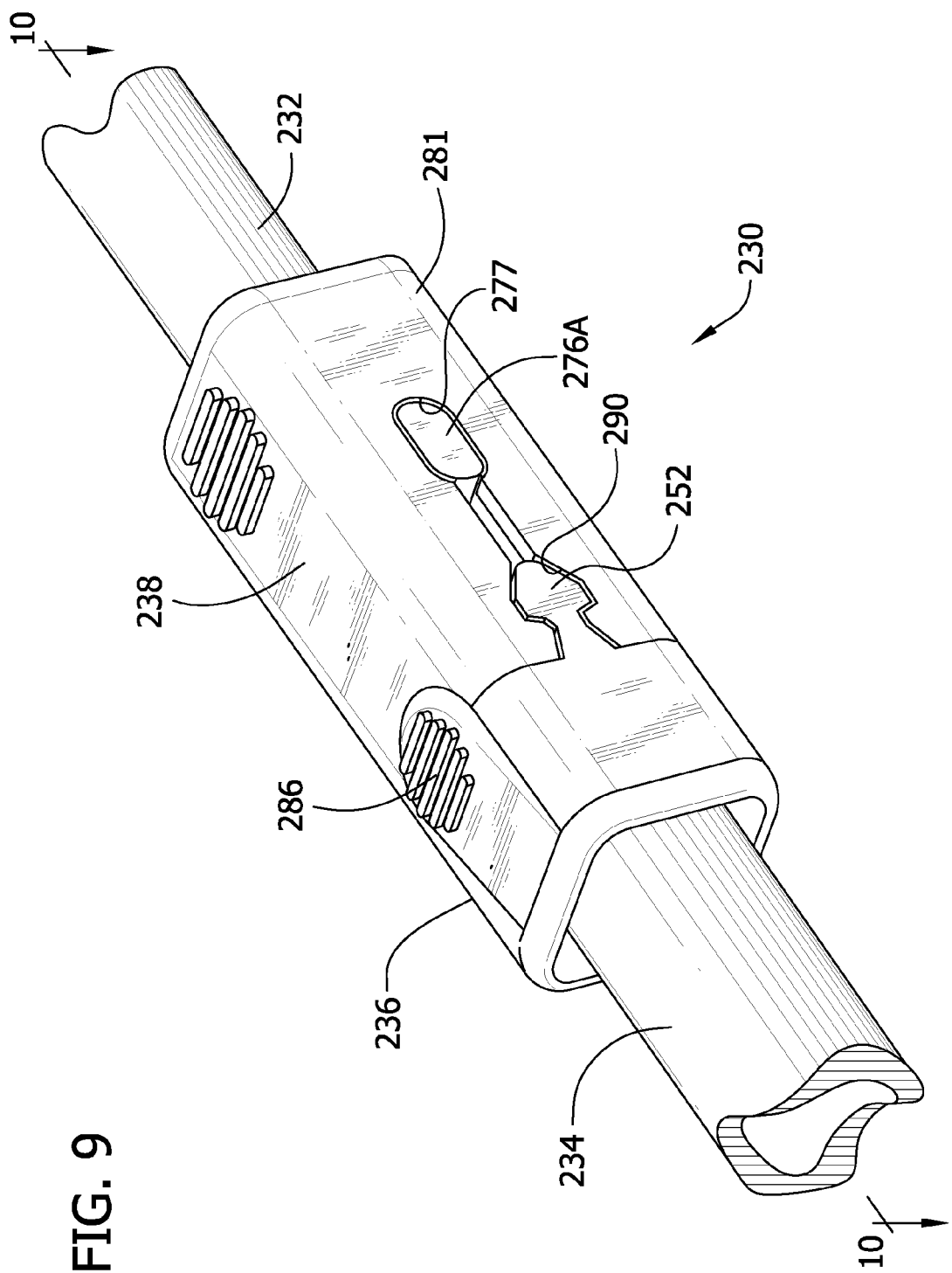
FIG. 9 is a perspective of another alternative embodiment of the connector assembly with tubing attached.
Figure 10:
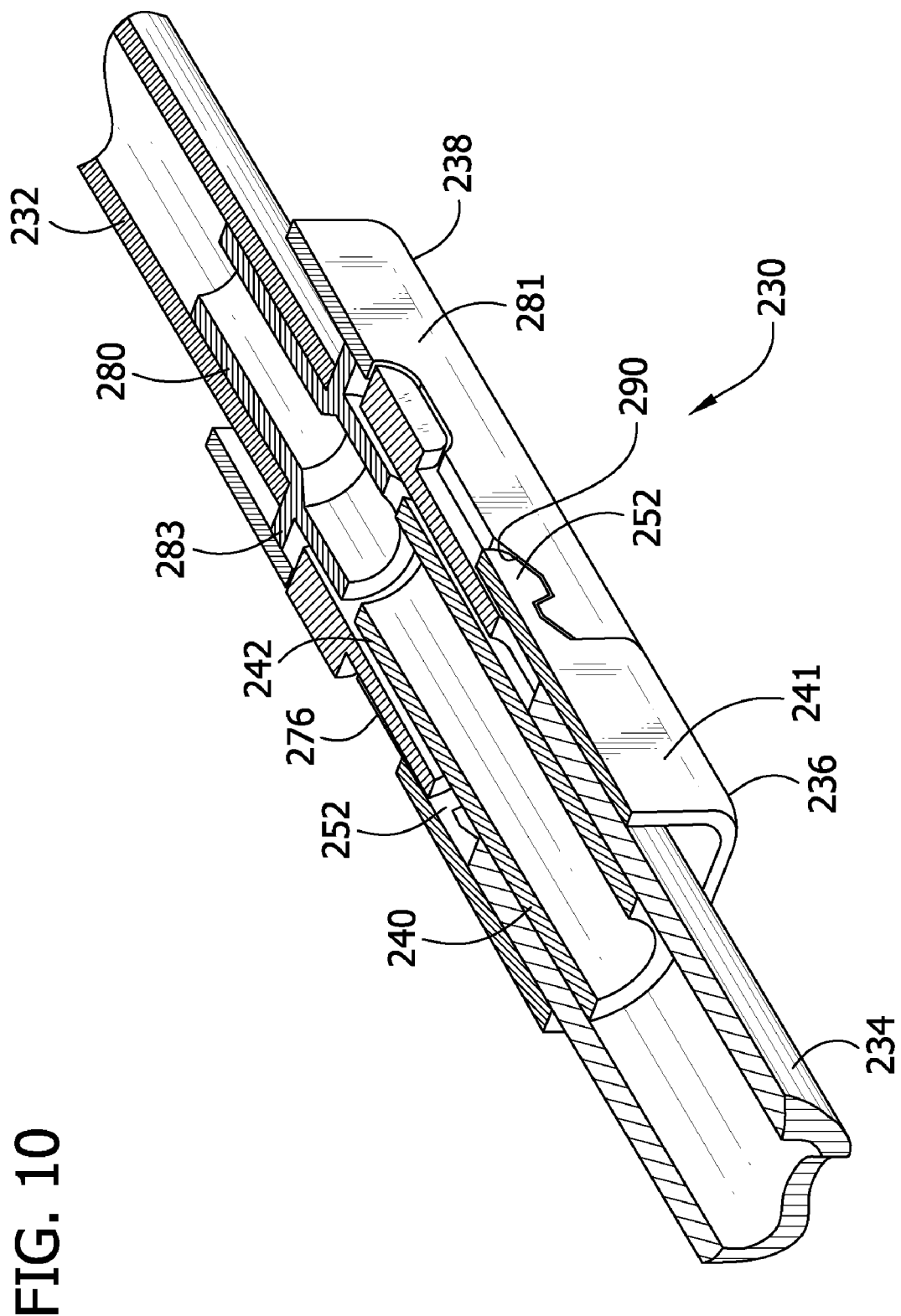
FIG. 10 is a perspective longitudinal section of the connector assembly as shown in FIG. 9.
Figure 11:
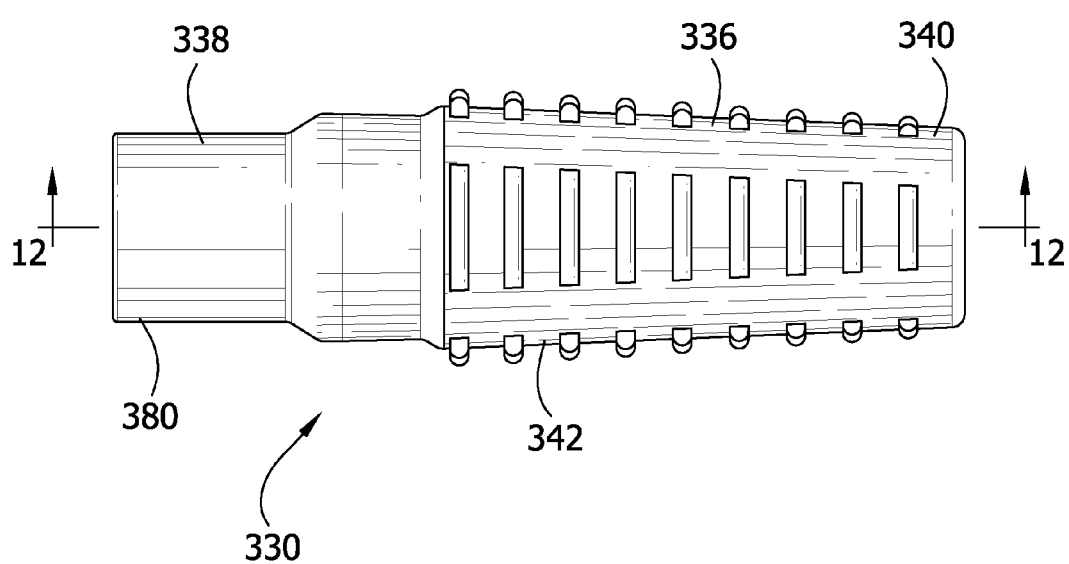
FIG. 11 is a side elevation of another alternative embodiment of the connector assembly with the first and second connectors engaged.
Figure 12:
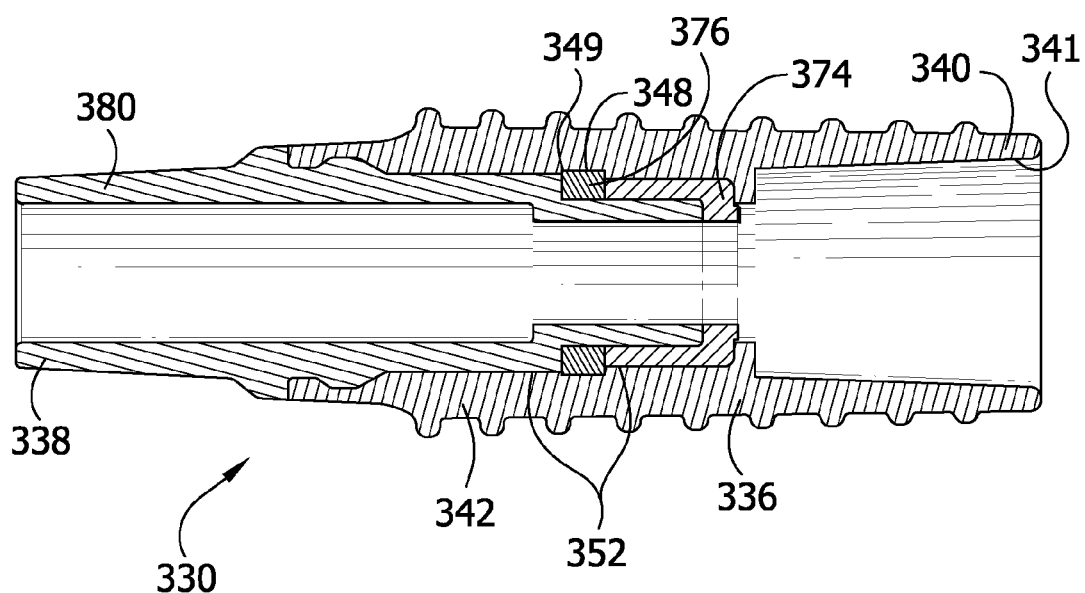
FIG. 12 is a longitudinal section of the connector assembly shown in FIG. 11.

FIGS. 9 and 10 illustrate a connector assembly 230 comprising a key 252 and a mating cavity 290. Parts of the connector assembly 230 corresponding to those of the connector assembly 30 are given the same reference numeral, plus "200." When the key 252 is positioned in the cavity 290, the user has established a fluid-tight seal within the connector assembly 230. The connector assembly 230 comprises a first connector 236 and a second connector 238. The first connector 236 has a tubular attachment portion 240 secured to an interior of a housing 241 of the first connector. The attachment portion 240 can be sealingly received in a (second) tubing 234. The second connector 238 has an attachment portion 280 that can attach the second connector to a (first) tubing 232. The second connector 238 includes a housing 281 that mounts the attachment portion 280 by way of a flange 283 of the attachment portion. A gasket 276 (broadly, "a sealing member") mounted by the housing 281 is generally tubular in shape and includes ears 276a that are received in correspondingly shaped openings 277 in the housing 281. The gasket 276 is received around and sealingly engages an exterior surface of the attachment portion 280 axially inward of the mounting flange 283.

Coupling portion 242 is slidingly and sealingly received by a first end of second connector 238 into the gasket 276 to form a sealing connection between the first and second connectors. The key 252 snaps into the mating cavity 290 to releasably lock the first and second connectors 236, 238 is sealing connection. To release the first connector 236, the user depresses a button 286, with raised edges, and pulls the first connector 236 from the second connector 238, while holding the second connector 238. Depressing the button 286 deforms the first connector and moves the key 252 laterally out of the cavity 290. The key 252 prevents engagement with a non-compliant connector (not shown).

Figure 19:
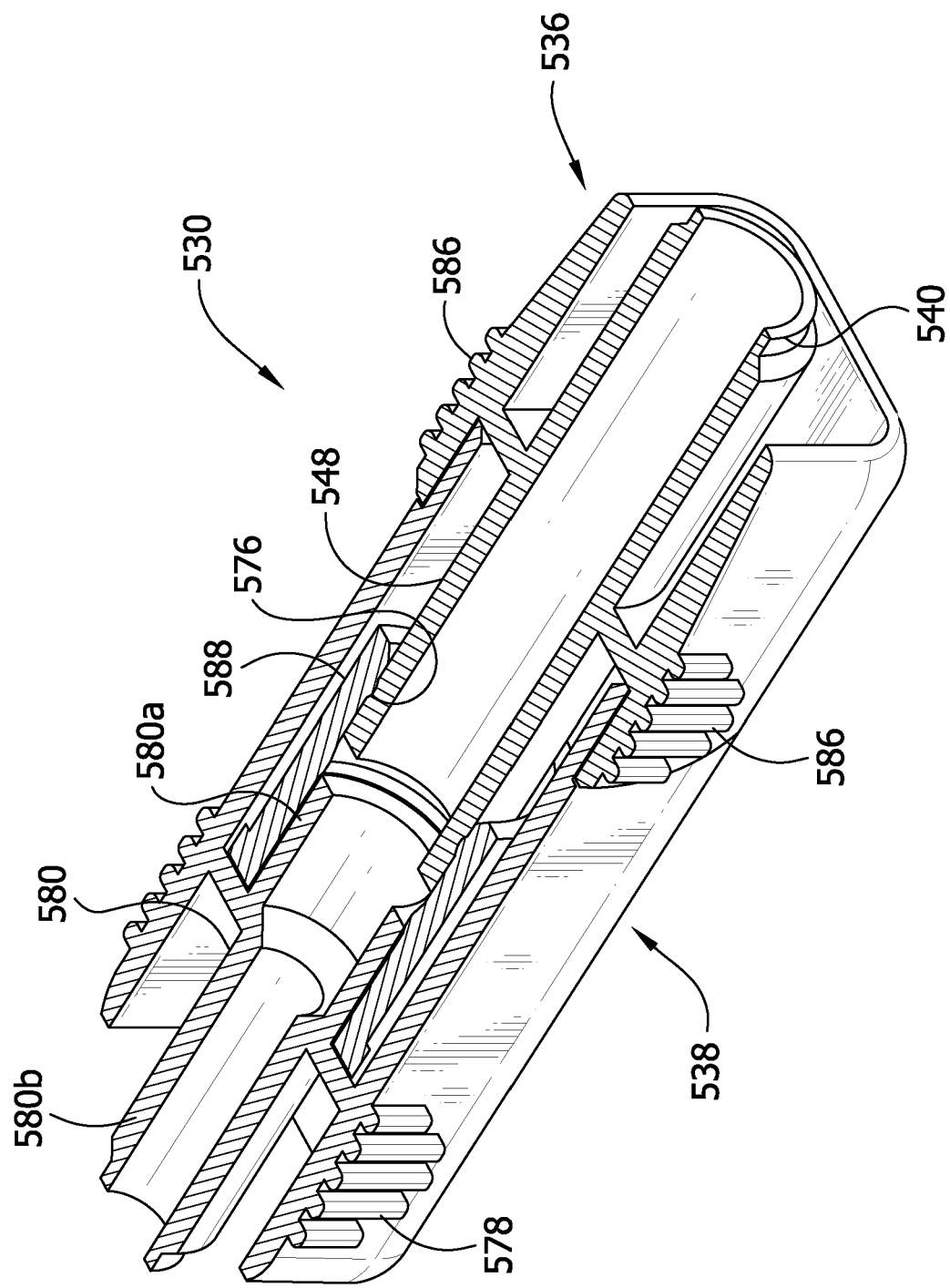
FIG. 19 is perspective longitudinal section of the engaged first and second connector of the connector assembly shown in FIG. 9.
Figure 19A:
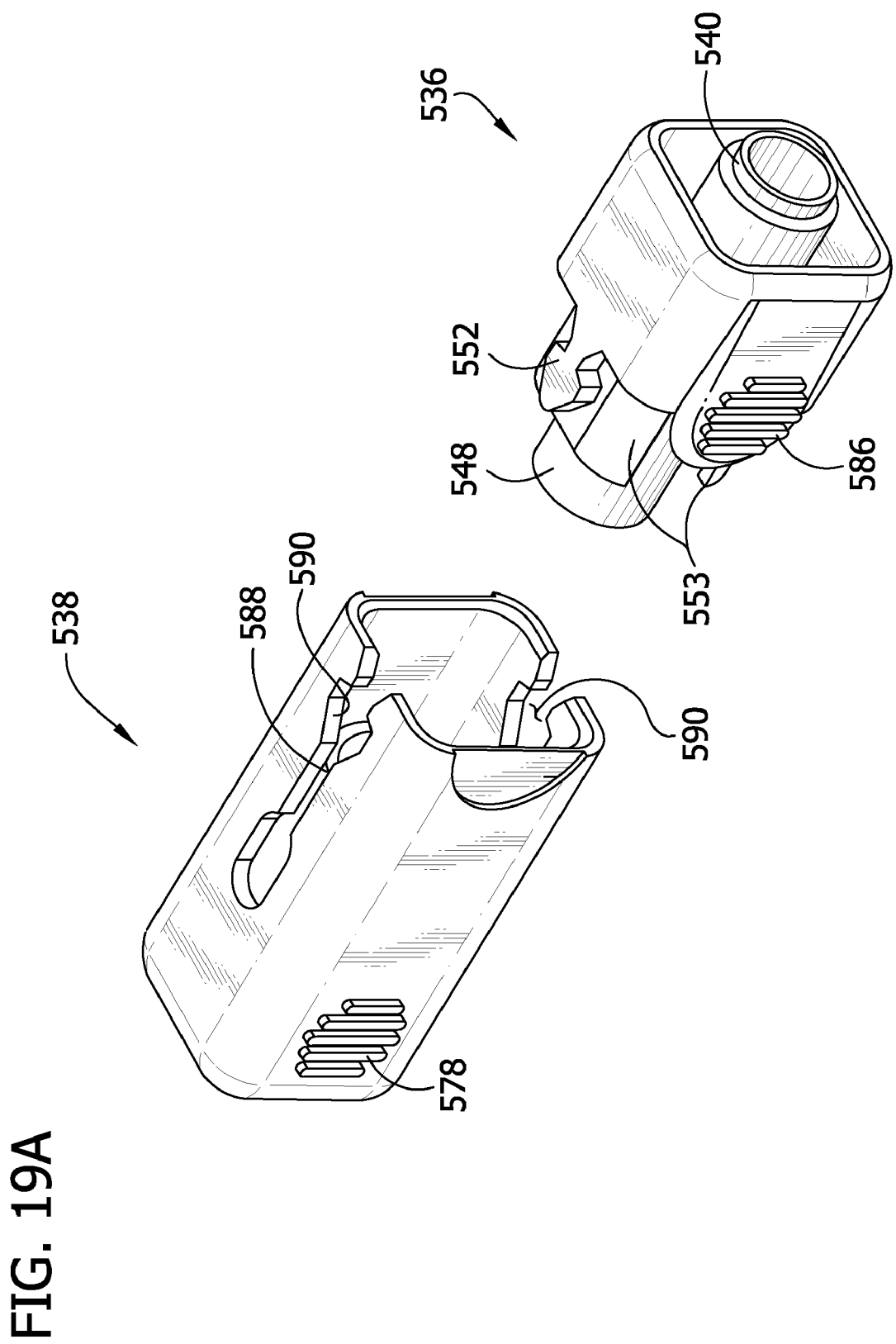
FIG. 19A is a perspective of the first and second connector separated of the connector assembly shown in FIG. 9.

An alternate embodiment of a keyed connector assembly 530 illustrated in FIGS. 19 and 19A is similar to the keyed connector assembly 230 of FIGS. 9 and 10. Parts of the connector assembly 530 corresponding to those of the connector assembly 30 are given the same reference numeral, plus "500." The first connector 536 comprises a key 552, guide flanges 553 and an inner rigid lumen or conduit 548 including an attachment portion 540. The second connector 538 comprises a mating cavity 590, an inner sealing member 588, and finger grips 578 An attachment portion 580 located within the second connector 538 includes an inner part 580a that is sealingly attached to the sealing member 588, and an outer part 580b that can be attached to tubing (not shown). In operation, the user grips the second connector 538 at the finger grips 578, grips the first connector 536 and then pushes the key 552 toward the cavity 590 until it snaps into the cavity. The flanges 553 engage the second connector 538 and help guide the first connector 536 into sealing engagement with the second connector. The inner end of the conduit 548 is received in the sealing member 588 and seals with the sealing member by engagement with an annular protrusion 576 in the sealing member. In this way, a sealing connection of the first and second connectors 536, 538 can be made.

Figure 13:
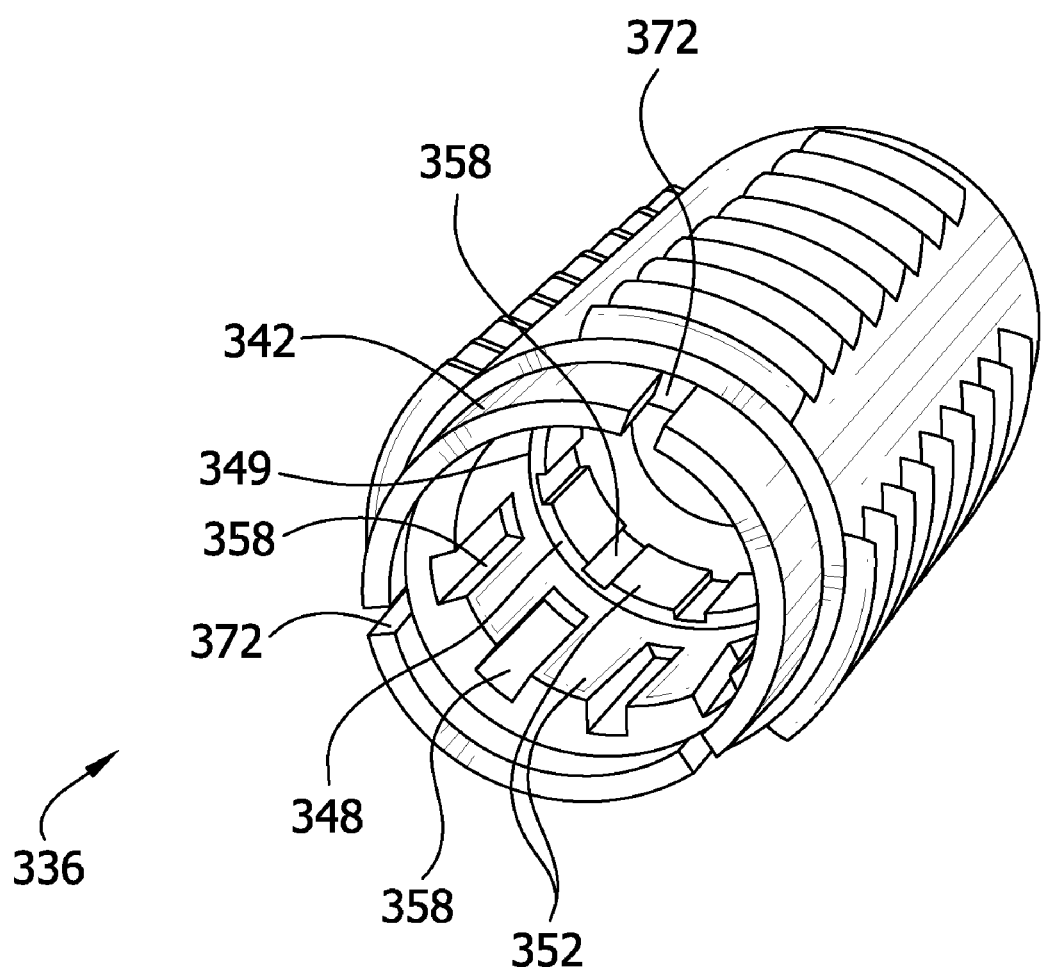
FIG. 13 is a perspective of the first connector of the connector assembly shown in FIG. 11.
Figure 14:
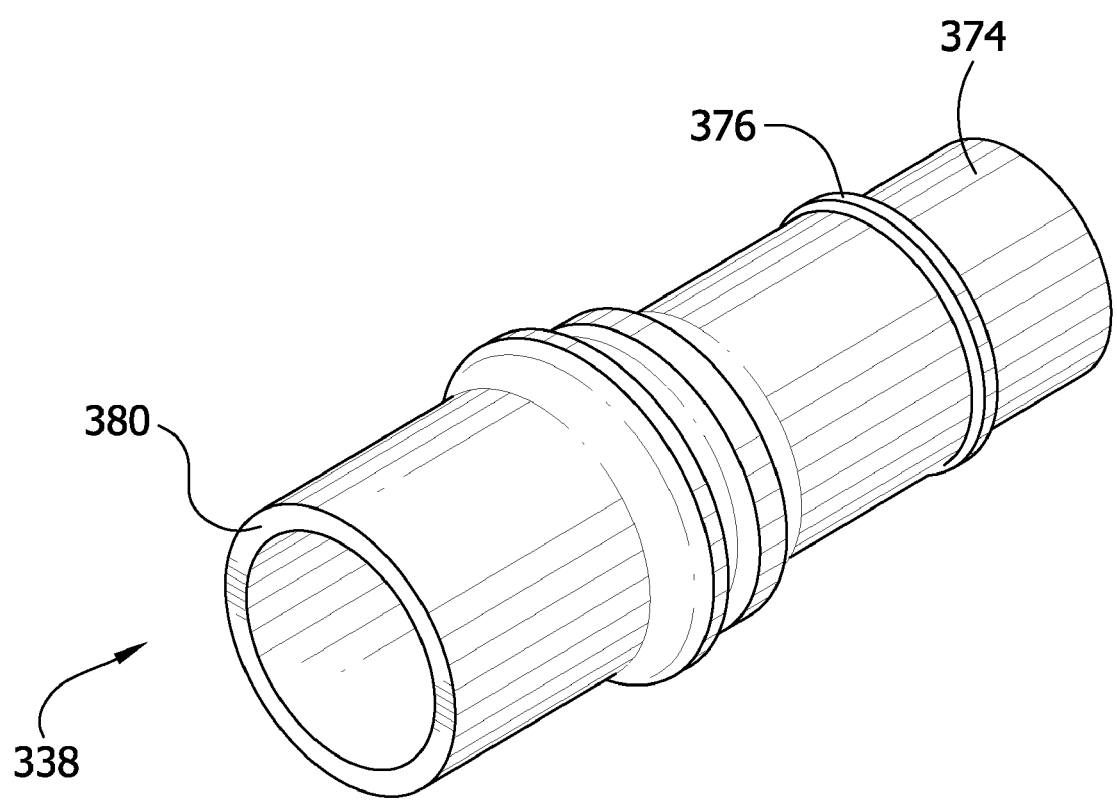
FIG. 14 is a perspective of the second connector of the connector assembly shown in FIG. 11.
Figure 15:
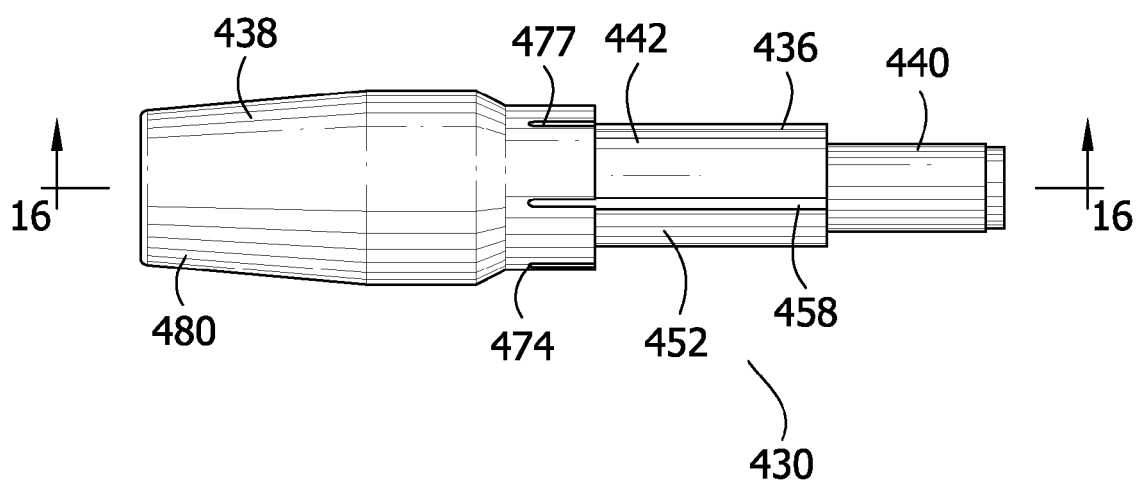
FIG. 15 is a side elevation of another alternative embodiment of the connector assembly with the first and second connectors engaged.

FIGS. 11-14 illustrate still another alternate embodiment of a connector assembly 330. Parts of the connector assembly 330 corresponding to those of the connector assembly 30 are designated by the same reference numerals, plus "300." Connector assembly 330 comprises a first connector 336 (FIG. 13), and a second connector 338 (FIG. 14). First connector 336 has an attachment portion 340 (FIG. 12) that accepts tubing (not shown) on the inner surface 341 of the attachment portion 340. The second connector 338 (FIG. 14) has an attachment portion 380 at a first end and a cap 374 at the second end. A second tubing (not shown) can be received on attachment portion 380. Spaced a distance from the second end is a deformable O-ring 376 around the perimeter of the cap 374. The O-ring 376 is releasably attached to the cap 374. It will be understood that a sealing member can be formed in any suitable manner such as an O-ring (as shown) or a raised surface of deformable plastic.

The first connector 336 further comprises a coupling portion 342 with at least one longitudinal channel 372 therethrough (FIG. 13). A plurality of non-sealing surface 352 areas (FIGS. 12 and 13) are disposed on the inside of the coupling portion 342. The non-sealing surfaces 352 have longitudinal channels 358 disposed on the inner surface of the first connector 336 to prevent a fluid seal with a non-compliant connector. The axially inner longitudinal channels 358 are also disposed on both sides of a groove 349 that defines the sealing surface 348 (FIG. 13). At the face of the coupling 342 are disposed a plurality of longitudinal channels 372 (FIG. 13). The open space defined by the channels 372 prevents the coupling portion 342 from forming a fluid seal with a surface of a non-compliant connector.

In operation, the user inserts the cap 374 into the opening at the coupling portion 342. The O-ring 376 is deformed as it moves over the non-sealing surfaces 352 under the force of the user. The O-ring 376 comes to rest in the groove 349 and engages the sealing surface 348 (FIG. 13), to form a fluid tight seal.

FIGS. 15-18 illustrate a further embodiment of a connector assembly 430. Parts of the connector assembly 430 corresponding to those of the connector assembly 30 are given the same reference numerals, plus "400." Connector assembly 430 includes a first connector 436 and a second connector 438. The first connector 436 has an attachment portion 440 that can be attached to a lumen (not shown) which fluidly communicates with a fluid source. A lumen (or tubing) is received on an outer surface of attachment portion 440 and forms a fluid-tight seal therewith. The first connector 436 has a coupling portion 442 comprising a sealing surface 448 and a pair of non-sealing surfaces 452 and each non-sealing surface 452 having longitudinal channels 458 (FIG. 17) disposed on the inner and outer surfaces of the coupling portion 442. The longitudinal channels 458 are disposed on either side of the sealing surface 448. The longitudinal channels 458 prevent a sealing engagement with the coupling portion 442 by a non-compliant connector. A longitudinal channel 458 can be oriented anywhere along the perimeter of the coupling portion 442 and can be of varying length, width or depth. A generally annular detent 479 (broken by channels 458) extends around the first connector 436.

The non-sealing surface 452 includes a first face 464. The first face 464 includes a transverse wall 468 that extends across the diameter of coupling portion 442. Transverse wall 468 is configured to prevent sealing engagement of the surface of coupling portion 442 with a non-compliant connector.

Figure 16:
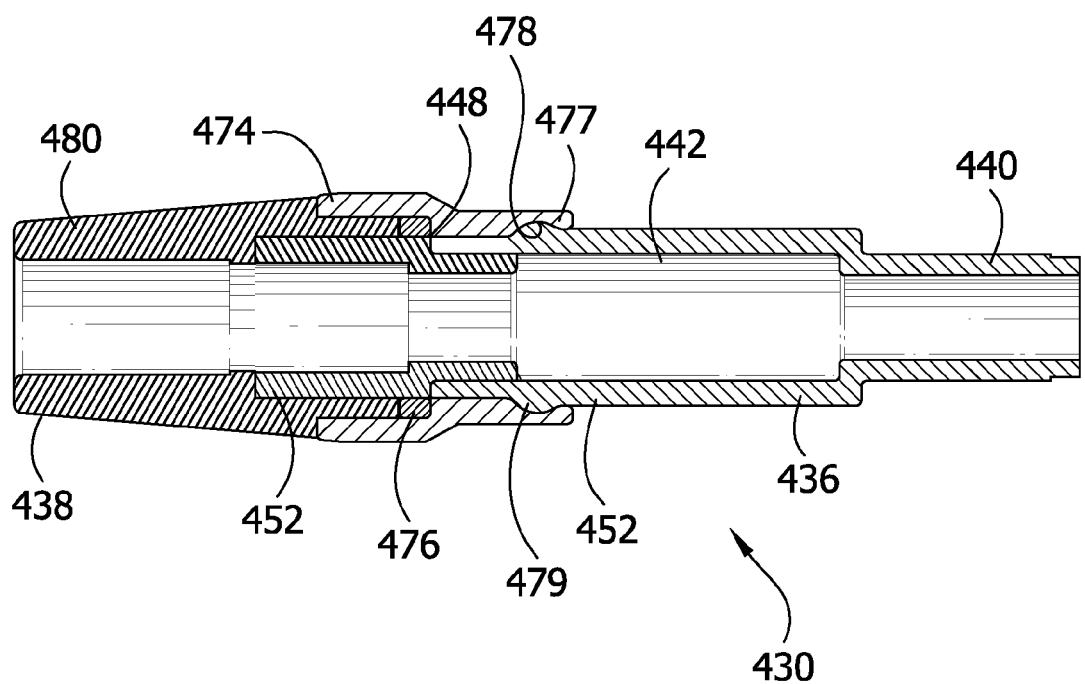
FIG. 16 is a longitudinal section of the connector assembly shown in FIG. 15.
Figure 17:
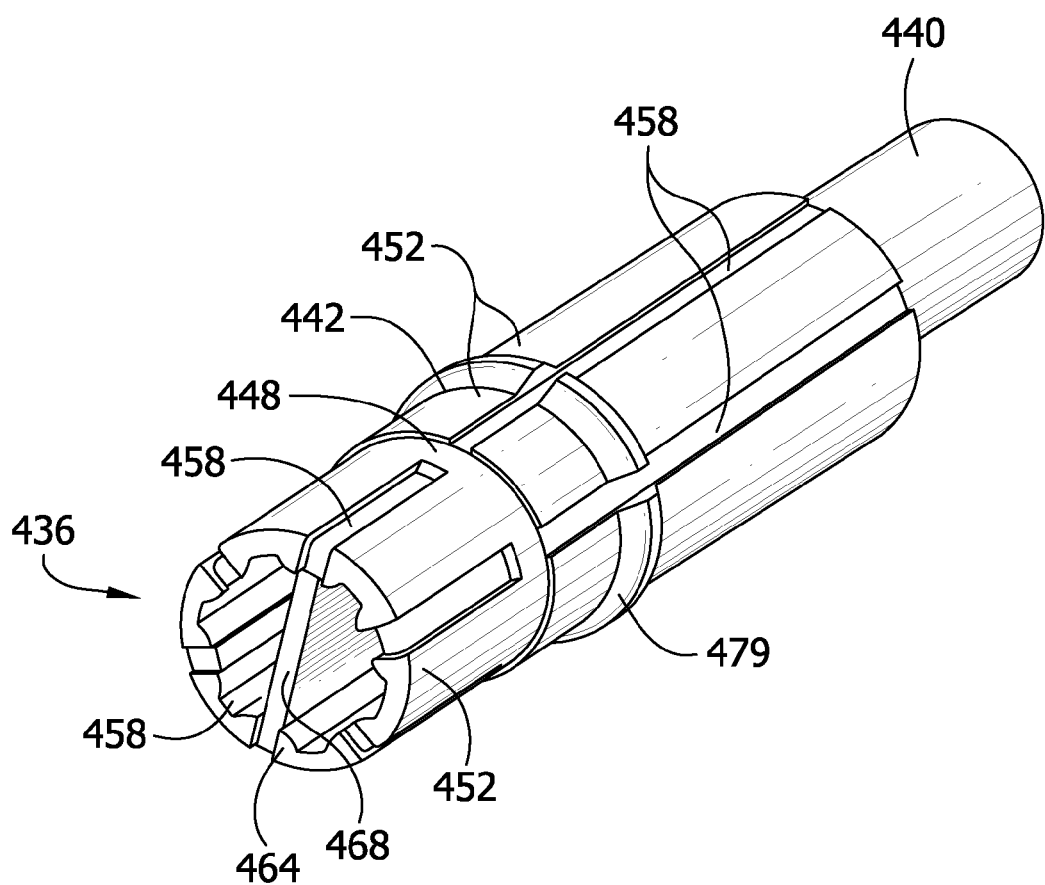
FIG. 17 is a perspective of the first connector of the connector assembly shown in FIG. 15.
Figure 18:
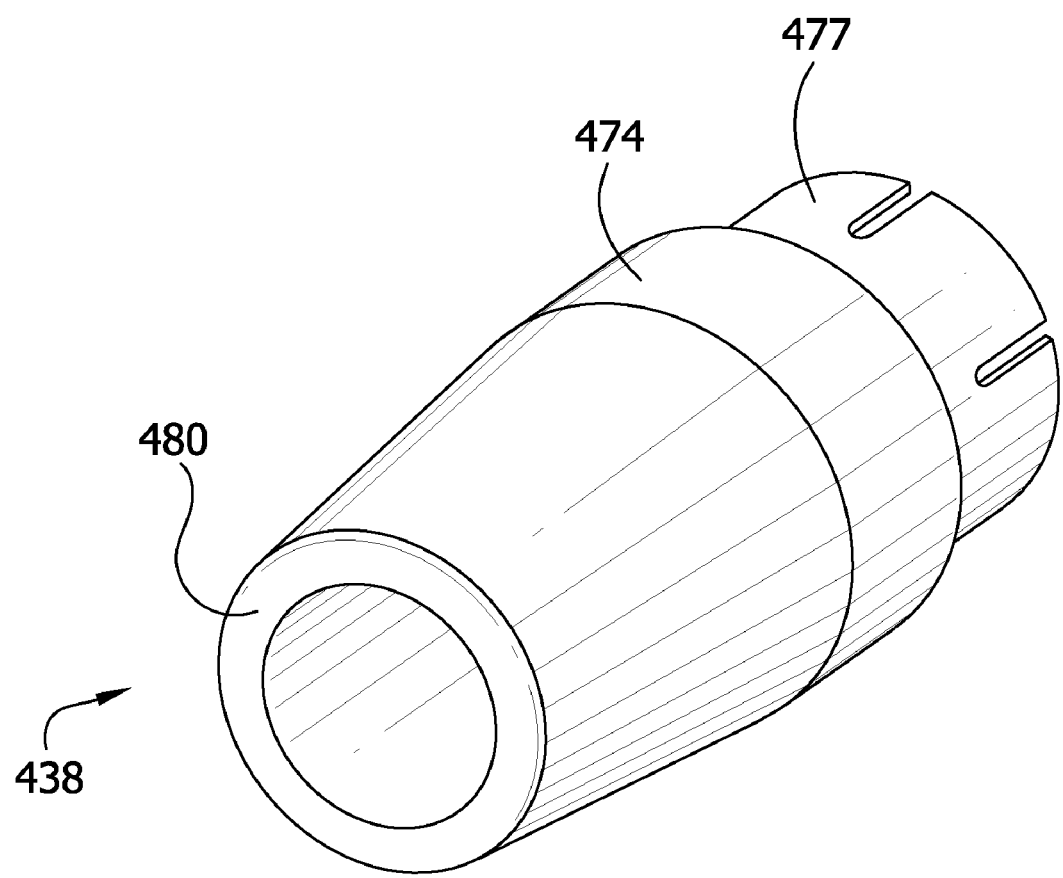
FIG. 18 is a perspective of the second connector of the connector assembly shown in FIG. 15.

The second connector 438 comprises an attachment portion 480, a cap 474, an O-ring 476 inside the cap and sealingly mounted on the cap, and a flex collar 477 (FIGS. 16 and 18). In operation, the user pushes the second connector 438 onto the coupling portion 442, with the first face 464 entering the opening of the second connector 438, at the flex collar end. The O-ring 476 engages the leading non-sealing surface 452 and does not establish a sealing connection with the non-sealing surface because of the channels 458. The O-ring 476 next engages the sealing surface 448 as the first connector 436 is advanced farther into the second connector 438 and establishes a sealing connection between the first and second connectors. The detents 479 of the first connector 436 are received in annular grooves 478 on the interior of the flex collar 477. The flex collar, which has been deflected from its relaxed position, bears against the detents 479 and holds them in the grooves 478 for securing the first and second connectors 436, 438 together.

FIGS. 20-25 illustrate a further embodiment of a connector assembly 630. Parts of the connector assembly 630 corresponding to those of the connector assembly 30 are given the same reference numerals, plus "600." The connector assembly 630 includes a first connector 636 and second connector 638. The first connector 636 includes a first housing 657, attachment portion 640, and coupling portion 642 and the second connector 638 includes a second housing 659, attachment portion 680, and receptacle 678. The first and second housings 657, 659 are removed in FIGS. 22 and 23 to better illustrate other features of the first and second connectors 636, 638. The first connector 636 may be integral with or secured to another object or device such as a wall 643 (only a fragmentary portion being illustrated) of the housing of a controller like the controller 2 shown in FIG. 41. The attachment portion 640 of the first connector 636 accepts tubing (not shown, but like medical tubing 32) that extends from the pump within the controller. However, the attachment portion 640 could be directly connected to an object other than tubing Referring to FIG. 22, the coupling portion 642 of the first connector 636 has a first end 644 and a second end 646. The second end 646 is suitably attached to the attachment portion 640, such as by solvent bonding or RF welding, or may be formed as one piece of material with the attachment portion. The attachment portion 640 may be sealingly received in tubing (e.g., tubing 32 of the tube set 20 (FIG. 42)). The coupling portion 642 includes a sealing surface 648 and a non-sealing surface 652. The non-sealing surface 652 is closer to the free end of the first connector 636 than the sealing surface 648. The sealing surface 648 extends around the perimeter of the coupling portion 642 at the second end 646. The shape and contour of the coupling portion 642 is not restricted to that of the illustrated embodiment, so long as the coupling portion can engage and form a seal with the second connector 638, as will be described. The non-sealing surface 652 has a greater diameter than the sealing surface 648. A number of circumferentially spaced channels 658 in the non-sealing surface 652 extend lengthwise of the first connector 636. The channels 658 operate to inhibit the formation of a sealing connection with an interior surface of medical tubing.

Figure 23:
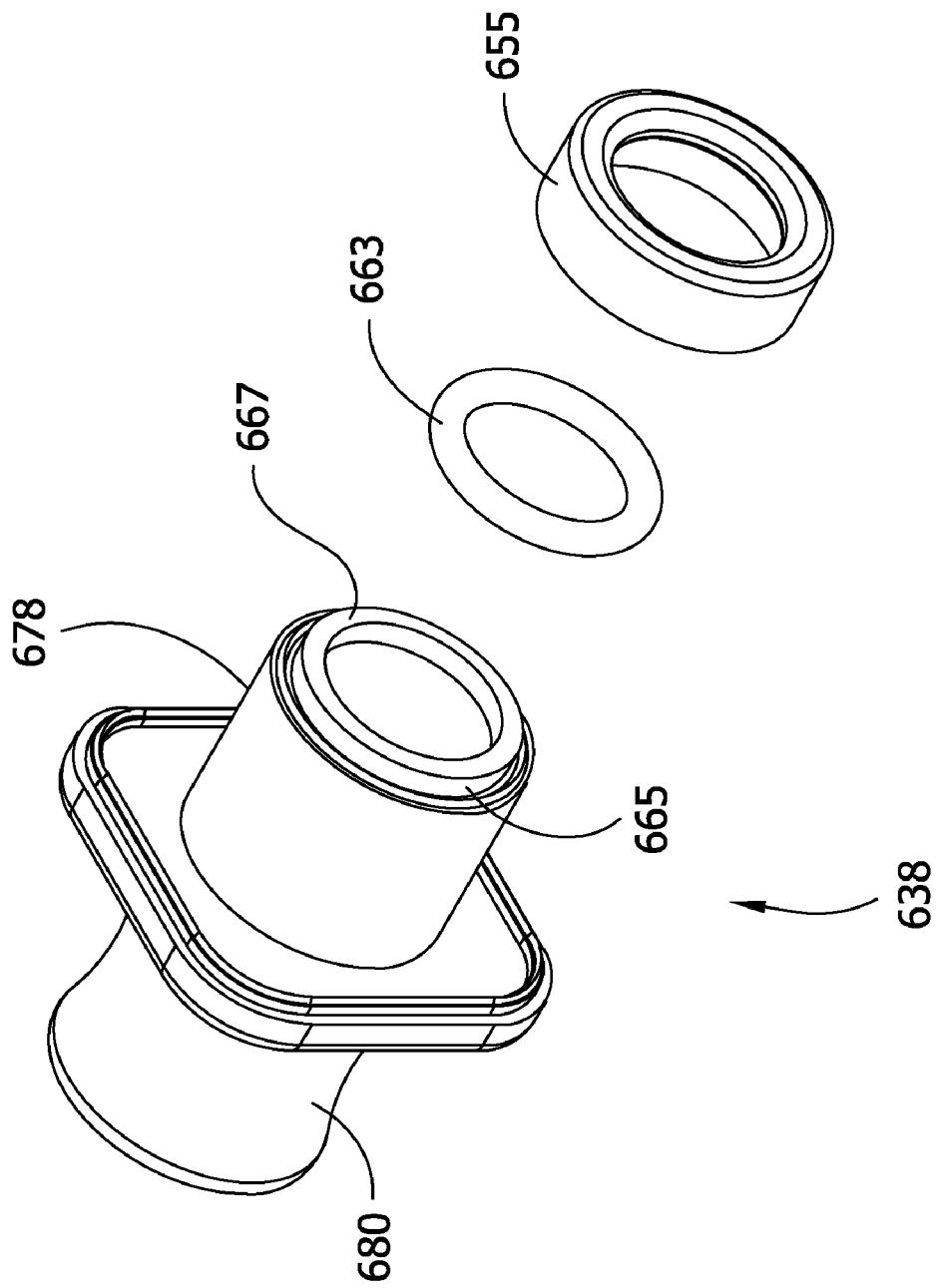
FIG. 23 is an exploded perspective of the second connector shown in FIG. 22.

The second connector 638 has a deformable O-ring 663 at the end of the receptacle 678 opposite the attachment portion 680, which is captured by a cap 655. Referring now to FIG. 23, the cap 655 fits over the O-ring 663 and makes a sna connection with a tapered end 665 of the receptacle 678 to capture the O-ring between the cap and the face 667 of the receptacle. Once captured, the O-ring 663 protrudes radially inward from between the end face 667 of the receptacle 678 and the cap 655 such that the O-ring can sealingly engage the sealing surface 648 of the first connector 636 when the first connector 636 is received in the second connector 638. The attachment portion 680 of the second connector 638 tapers in diameter toward its middle to facilitate gripping of the second connector assembly 639. The attachment portion 680 may sealingly receive generic tubing (e.g., tubing 32 of the tube set 20 (FIG. 42)).

Figure 20:
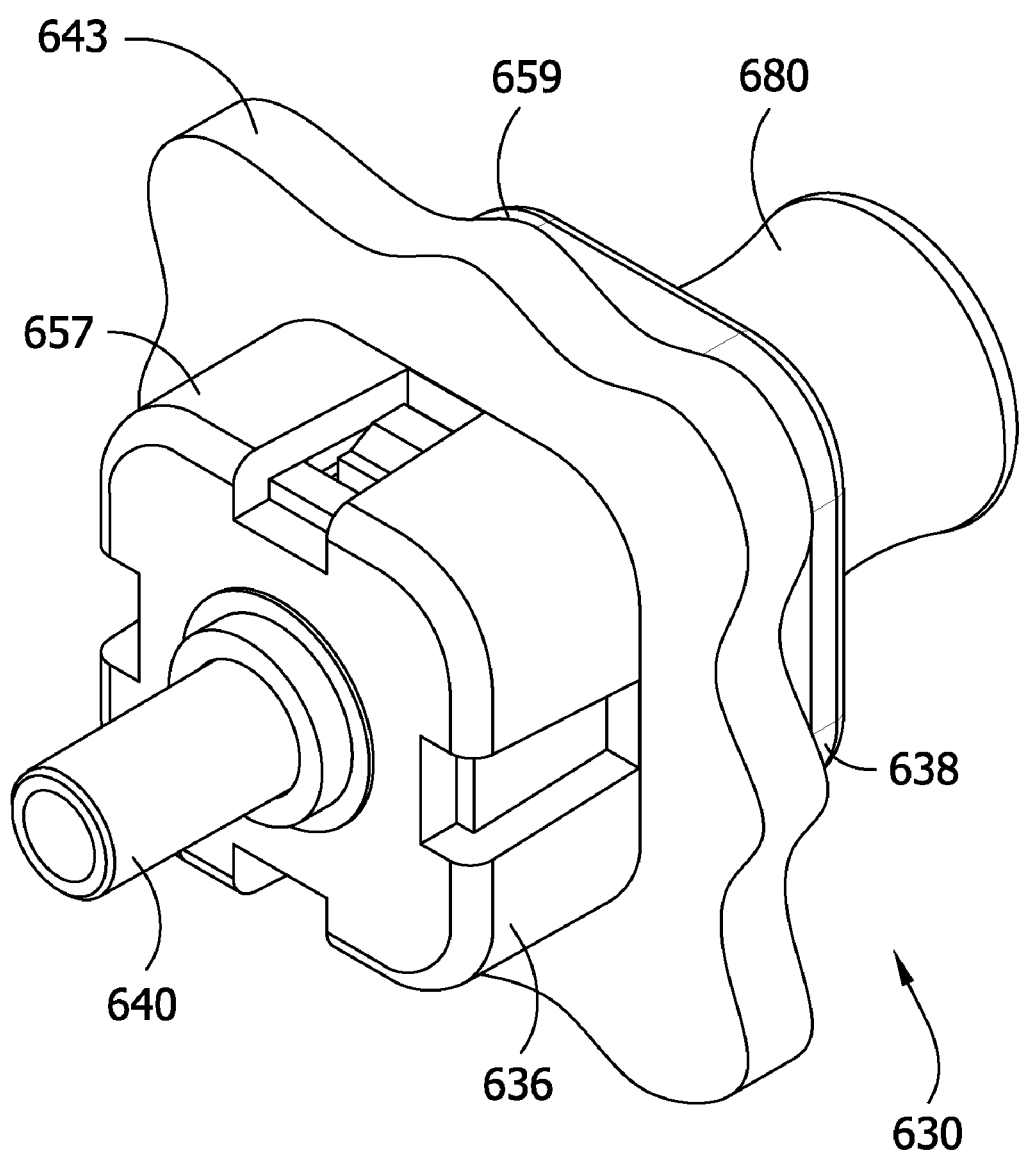
FIG. 20 is a perspective of an alternative embodiment of the connector assembly with first and second connectors of the connector assembly engaged.
Figure 21:
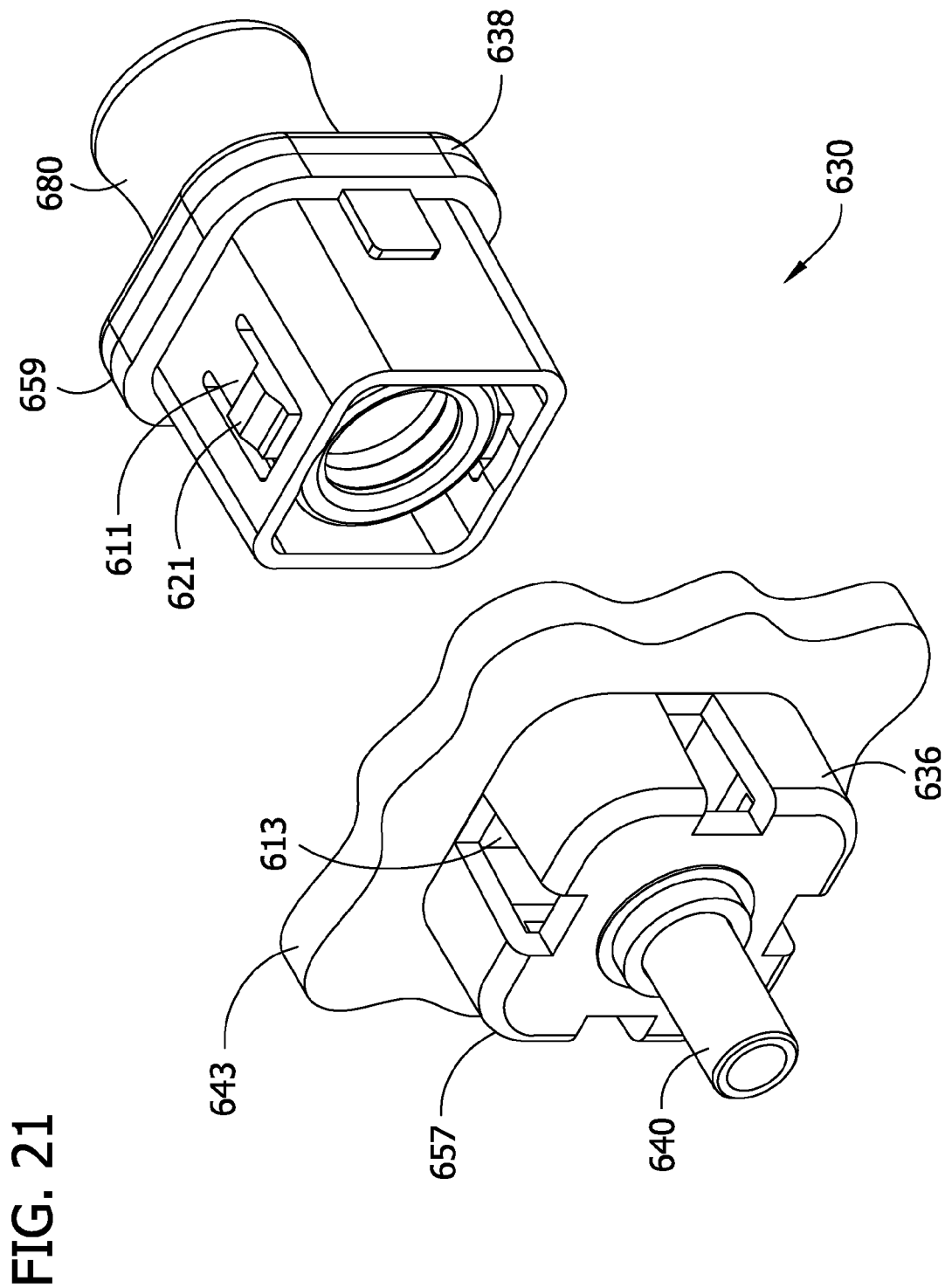
FIG. 21 is a perspective of the connector assembly with the first and second connectors separated.
Figure 22:
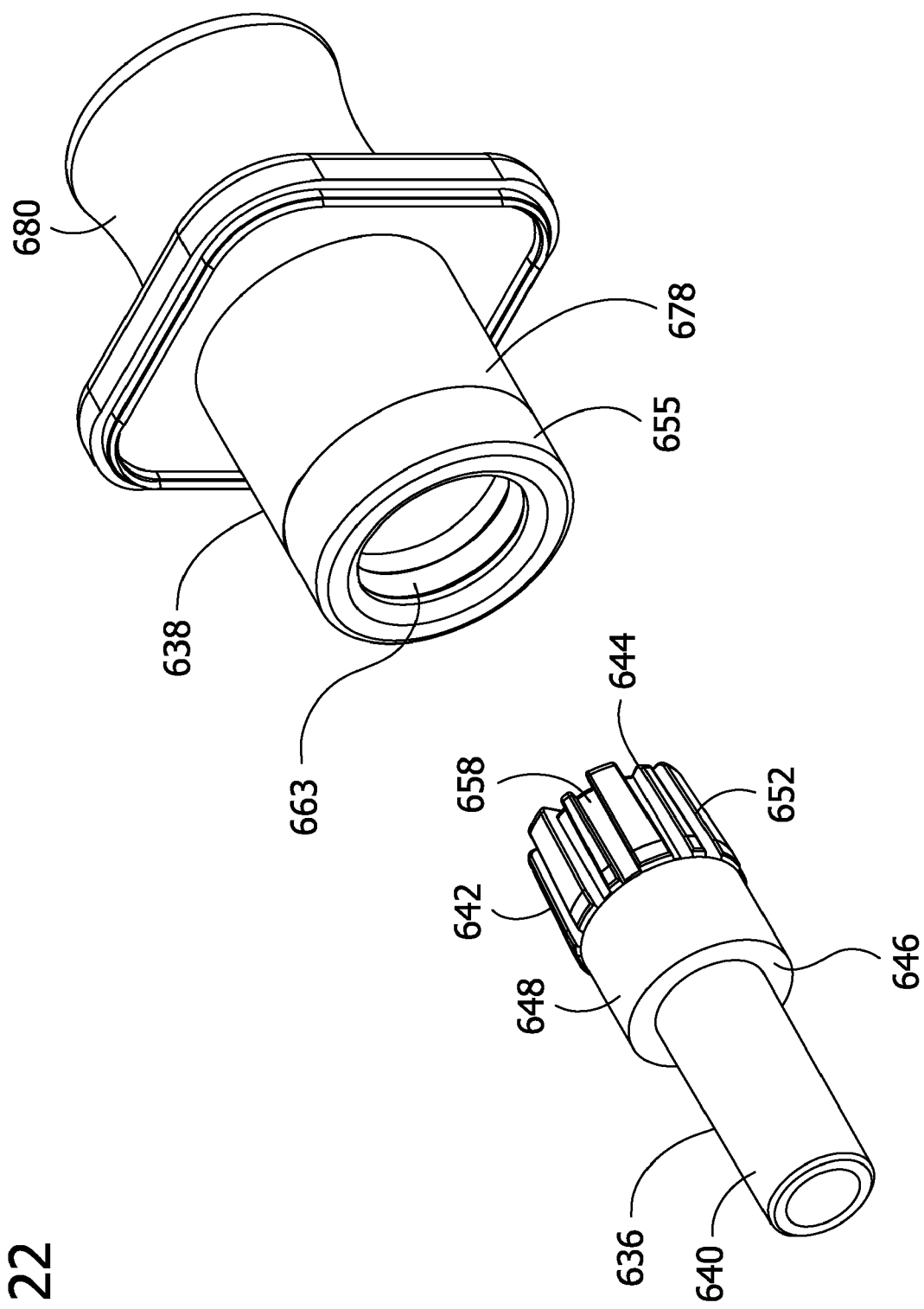
FIG. 22 is the perspective of FIG. 20 with the first and second housings removed.

Referring to FIGS. 20 and 21, the second connector 638 includes a key 611 having a projecting member 621. The first connector 636 includes a mating cavity 613. To form a seal between the first connector 636 and the second connector 638, the user must push the first end 644 of the first connector through the O-ring 663 and into the receptacle 678 of the second connector 638, such that the non-sealing surface 652 passes beyond the O-ring. When the key 611 of the second connector 638 639 is positioned in the mating cavity 613 of the first connector 636 to such an extent that the projecting member 621 abuts the first housing 657, the sealing surface 648 has engaged the O-ring 663. Abutment of the projecting member 621 and the first housing 657 prevents separation of the first connector 636 and the second connector 638. To release the second connector 638, the user depresses the projecting member 621 and pulls the first connector 636 from the second connector 638, while holding the second connector. Depressing the projecting member 621 moves the projecting member out of the mating cavity 613.

Figure 24:
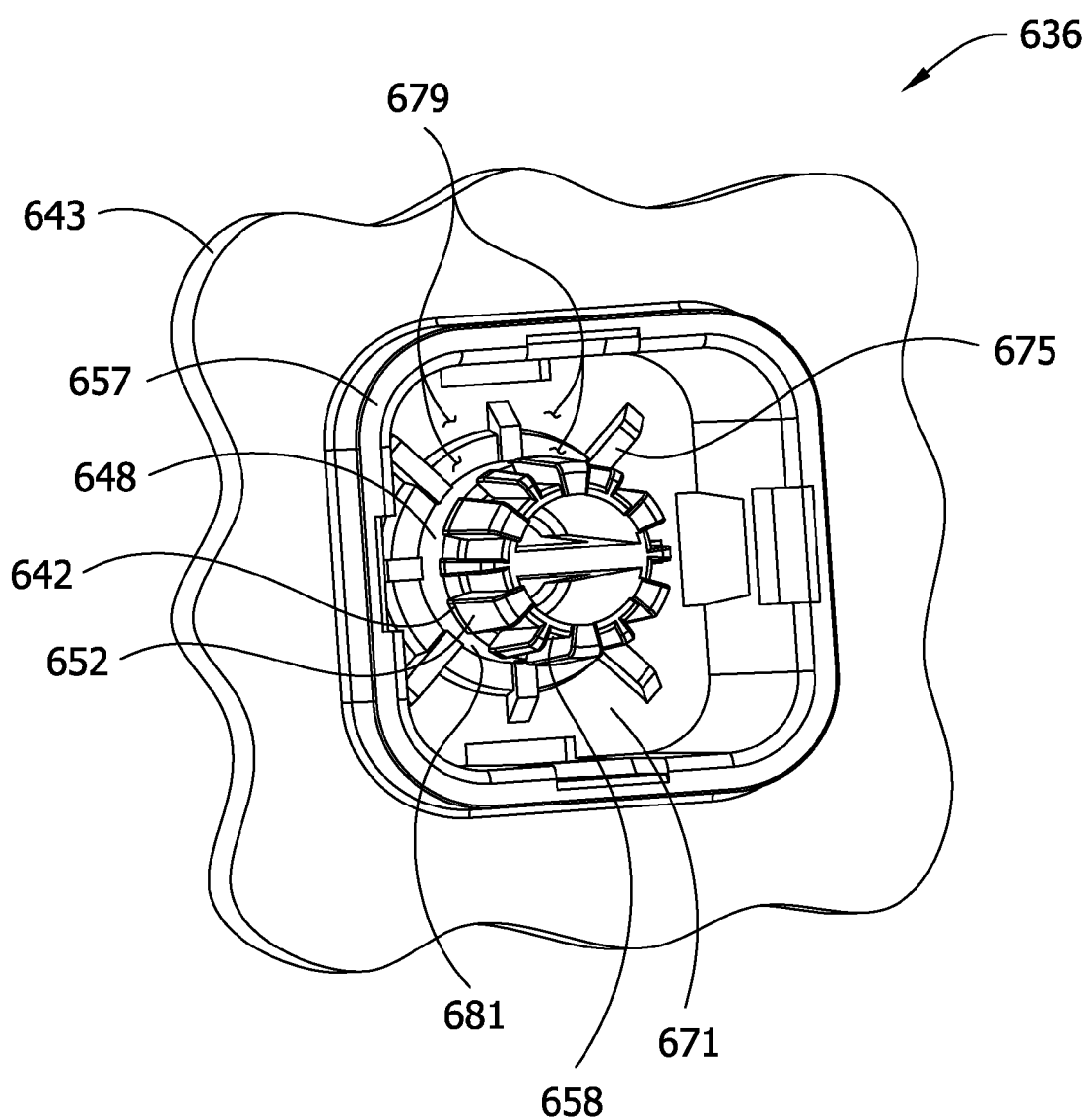
FIG. 24 is a perspective of the first connector assembly shown in FIG. 20.
Figure 25:
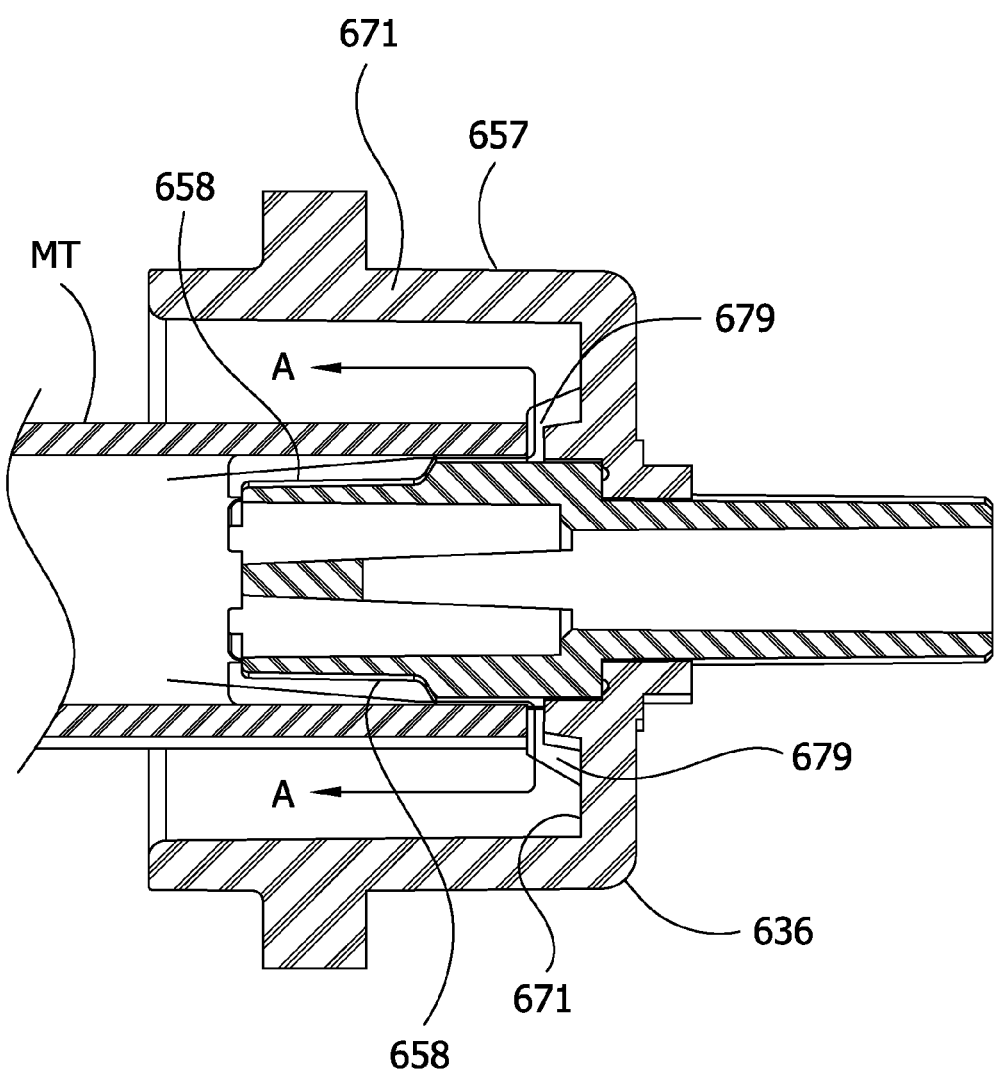
FIG. 25 is a longitudinal section taken through opposed channels of a non-sealing surface of the first connector shown in FIG. 24 showing attempted attachment of a non-permitted conduit.

Referring to FIGS. 24 and 25, the first housing 657 of the first connector 636 includes a floor 671. The coupling portion 642 projects outward from the floor 671. Standoff ribs 675 that project outward from the housing floor 671 are circumferentially spaced about the coupling portion 642. The end of each standoff rib 675 adjacent the coupling portion 642 is attached to a connecting segment 681 that circumferentially surrounds the coupling portion. Bleed passages generally indicated at 679 are defined beyond the connecting segments 681 and between the ribs 675 and floor 671. The bleed passages 679 extend past the end face of a conduit such as generic medical tubing, when the conduit is fully inserted onto the coupling portion 642 that allows fluid to be bled around the coupling portion to prevent a fluid-tight seal. The direction and pathway of flow is generally indicated by arrow "A" (FIG. 25). The bleed passages 679 prevent successful fluid-tight connection between the coupling portion and medical tubing MT (a "non-permitted conduit") when the end face of the medical tubing is pushed all the way into the first housing 657 as illustrated in FIG. 25. In this condition, a typical controller can sense the absence of the fluid tight connection and initiate an alarm.

Figure 26:
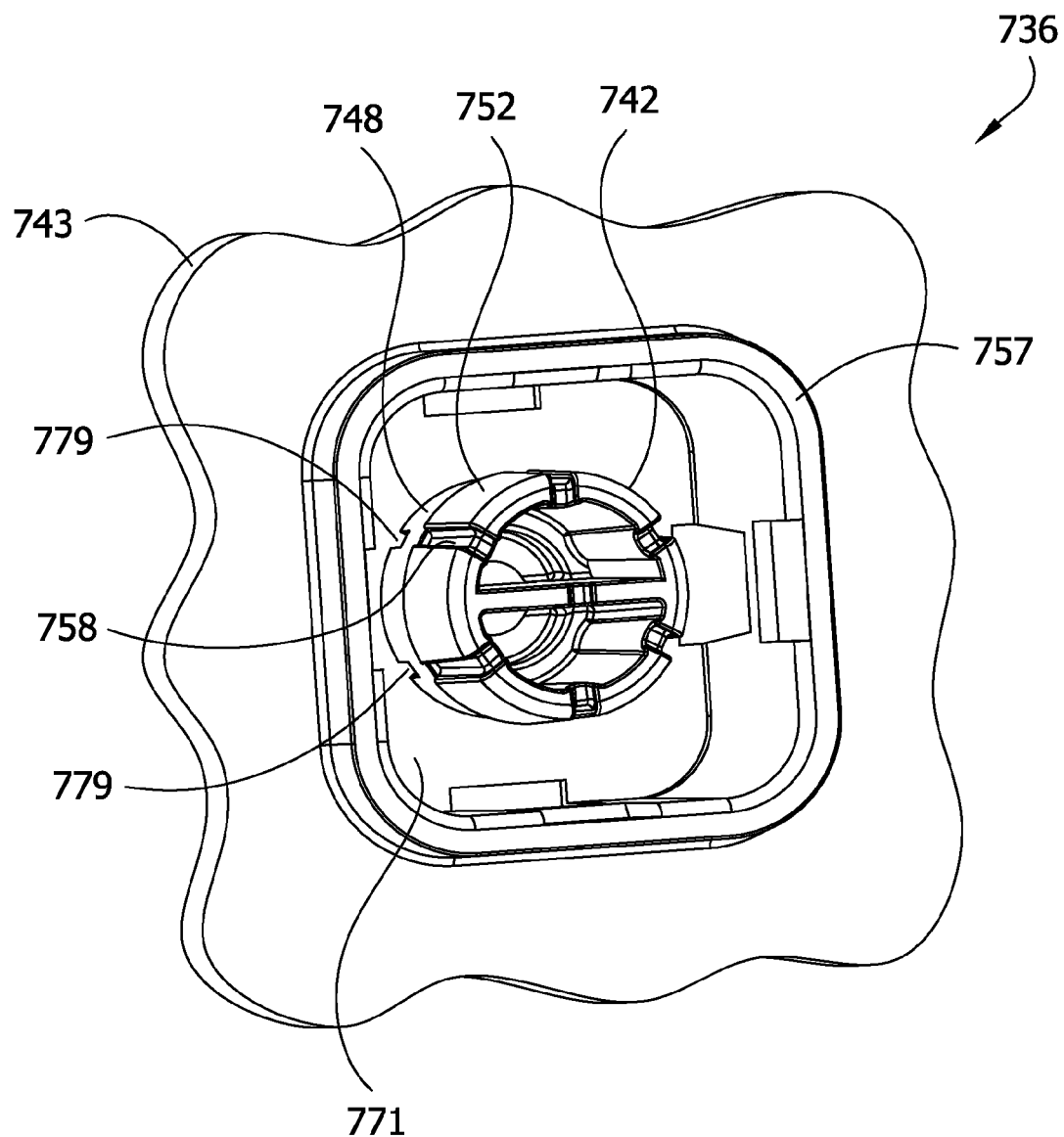
FIG. 26 is a perspective of an alternative embodiment of the first connector assembly.
Figure 27:
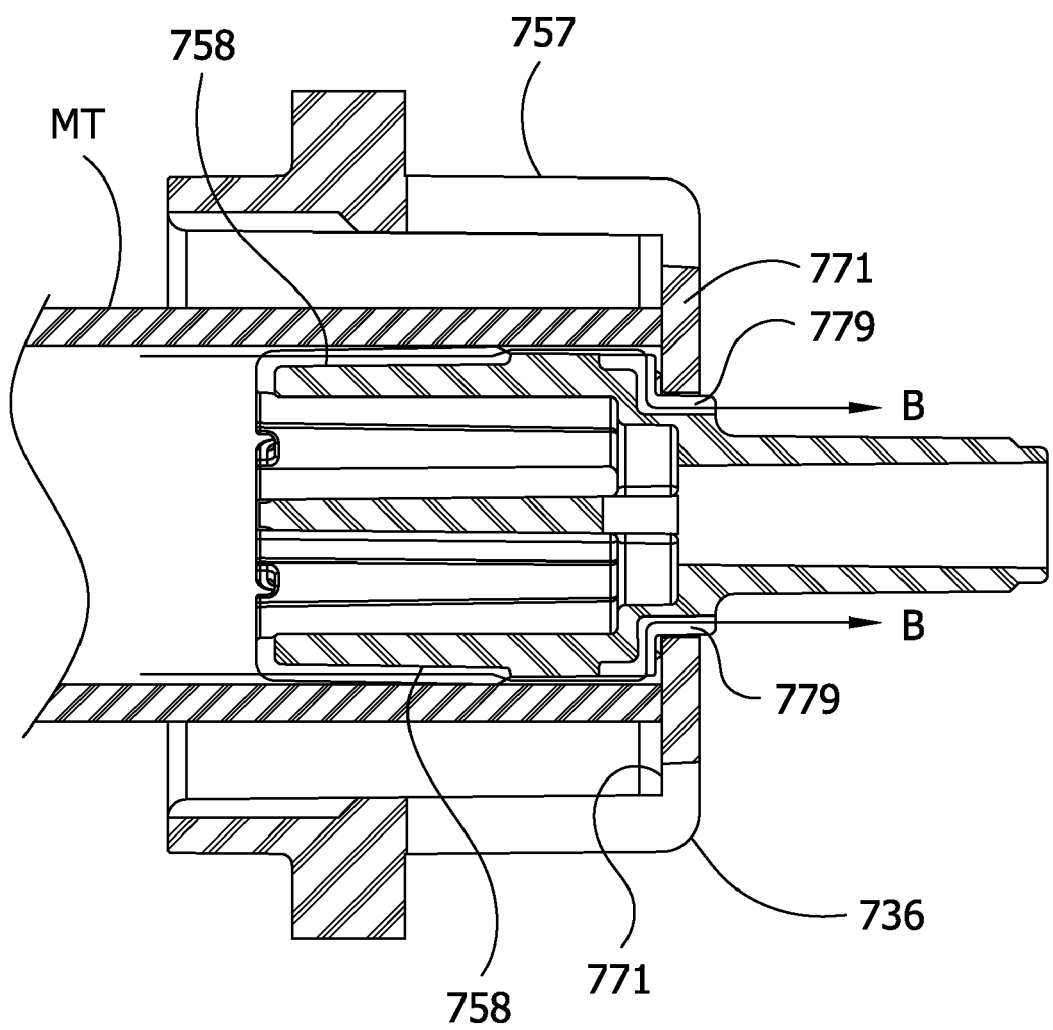
FIG. 27 is a longitudinal section taken through opposed channels of a non-sealing surface of the first connector shown in FIG. 26 showing attempted attachment of a non-permitted conduit.

FIGS. 26 and 27 illustrate a further embodiment of the first connector 736. Parts of the first connector 736 corresponding to those of the connector 636 are given the same reference numerals, plus "100." Bleed passages 779 are formed in the first connector 736 and located generally adjacent the floor 771 of the housing 757 for bleeding fluid around the coupling portion 742. Referring now to FIG. 26, the bleed passages 779 open radially outward of the coupling portion 742 at a first opening and extend axially through the housing floor 771 and open from the first connector at the side of the floor opposite the first opening. A non-sealing surface 752 of the coupling portion 742 holds conventional medical tubing MT (a "non-permitted conduit") from sealing with the sealing surface 748. An end face of the tubing MT may seal with the floor 771. However, the bleed passages 779 formed in the sealing surface 748 are not sealed. Thus, air in the medical tubing MT may pass through the channels 758 in the non-sealing surface 752, along the sealing surface 748 and out the bleed passages 779 as indicated by arrow "B" (FIG. 27). Therefore, no fluid-tight connection can be made with standard medical tubing MT, even if the end face of the tubing otherwise seals with the floor 771.

Figure 28:
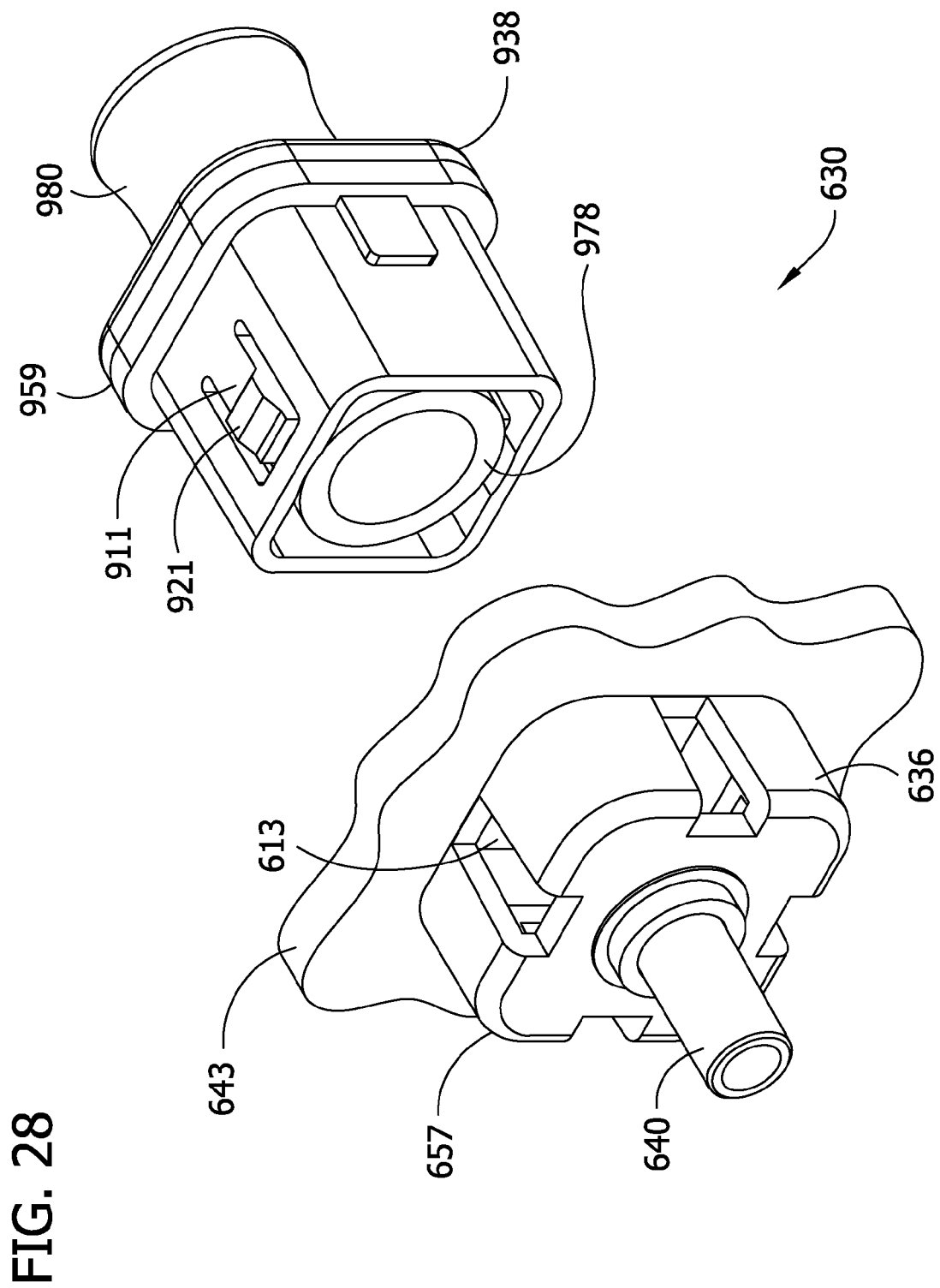
FIG. 28 is a perspective similar to FIG. 21 but showing a second connector of another embodiment.
Figure 29:
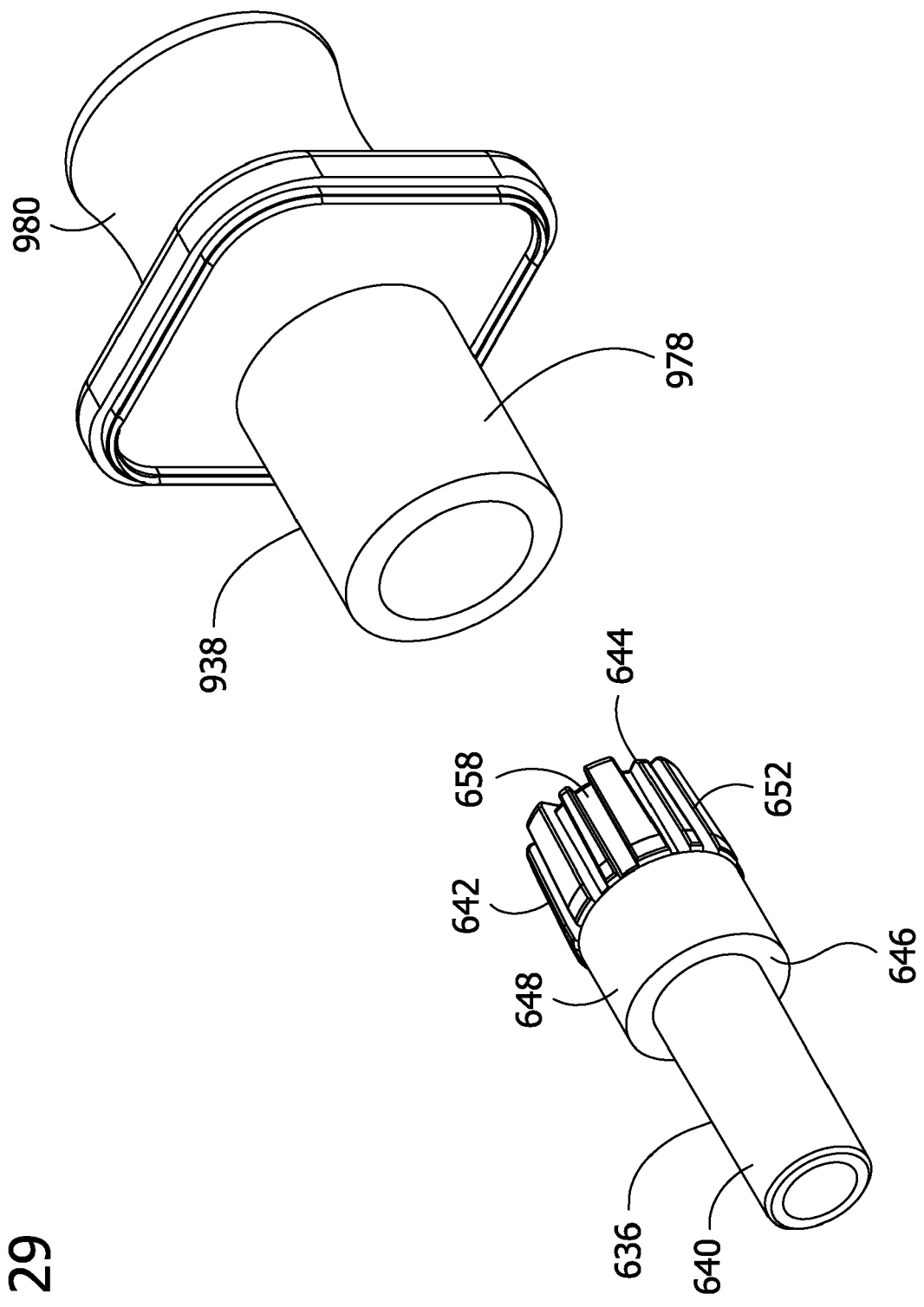
FIG. 29 is the perspective of FIG. 28 with the first and second housings removed.
Figure 30:
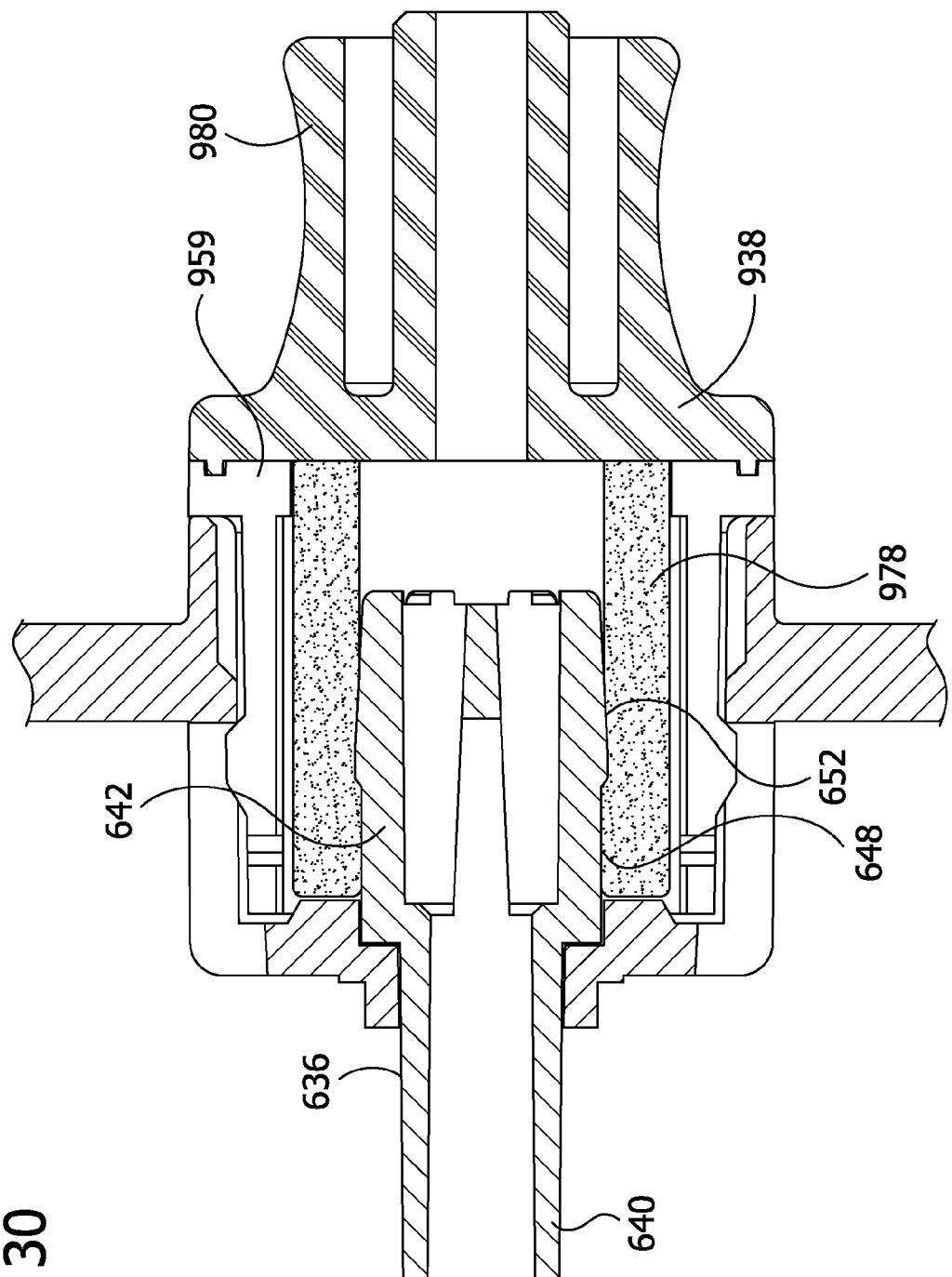
FIG. 30 is a longitudinal section through the mated first and second connectors of FIG. 28.

FIGS. 28-30 illustrate a further embodiment of the second connector 938. Parts of the second connector 938 corresponding to those of the connector 638 are given the same reference numerals, plus "300." The second connector 938 includes a second housing 959, attachment portion 980, and conduit 978. The first and second housings 657, 959 are removed in FIG. 29 to better illustrate other features of the first and second connectors 636, 938. The attachment portion 980 may sealingly receive and being sealingly joined to generic tubing (e.g., medical tubing 32 of the tube set 20 (FIG. 42)).

Referring to FIG. 29, the second connector 938 does not include a deformable O-ring, but, rather, the conduit (or "receptacle") 978 itself is adapted so that the open outer end is capable of receiving both the large diameter non-sealing surface 652 and the smaller diameter sealing surface 648 and is capable of forming a fluid-tight seal with the sealing surface upon connection of the first connector 636 and second connector 938. At least one of the hardness and the wall thickness of the conduit 978 must be selected such that the open outer end of the conduit receives the large diameter non-sealing surface 652 and forms a fluid-tight seal with the sealing surface 648. For example, it has been found that tubes made of polyvinylchloride (PVC) with a hardness of from about 50 durometer (type A) to about 70 durometer (type A) and a thickness of from about 50 mil to about 100 mil (about 1.27 mm to about 2.54 mm) are capable of receiving the large diameter non-sealing surface 652 and forming a fluid-tight seal with the sealing surface 648. In particular, these characteristics are selected to be different from standard medical tubing.

FIG. 30 illustrates a cross-section of the first connector 636 connected to the second connector 938. In the illustrated embodiment, the housing 959 is made of a material that is more rigid than the material of the conduit 978 and the conduit is mounted on the housing. As can be seen from FIG. 30, when mated with the first connector 636 the conduit 978 deforms itself over the non-sealing surface 652 and forms a fluid-tight seal with the sealing surface 648. The hardness and the wall thickness of the conduit 978 is selected so that it will deform into sealing engagement with the sealing surface 648 of the first connector 636 while remaining in engagement with the non-sealing surface 642, as shown in FIG. 30. Although in the illustrated embodiment, the first connector 636 is a male connector and the second connector 938 is a female connector, the roles could be reversed within the scope of the present invention. In that event, the conduit would be received inside a first connector.

While the second connector 938 is shown with a housing 959, the second connector may form the end of a tube and not have a housing or attachment portion 980 without departing from the scope of the present invention. For instance, the second connector 938 may form an end of the tubing 32 (FIG. 41) or the end of the second tubing 34 extending from the bladder 4 of the compression therapy device 1 (FIG. 40).

Figure 31:
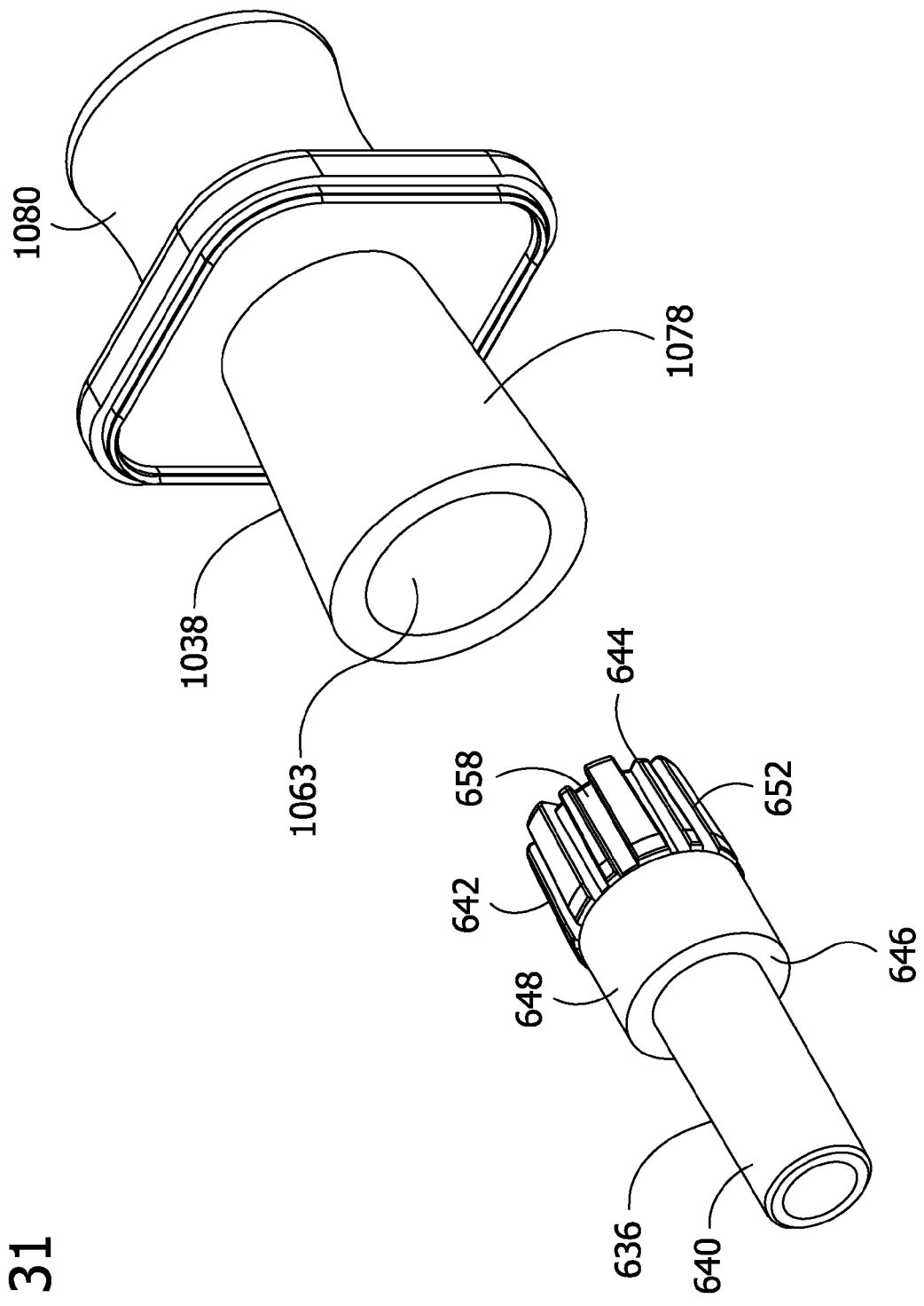
FIG. 31 is a perspective similar to FIG. 29, but showing a second connector of yet another embodiment.
Figure 32:
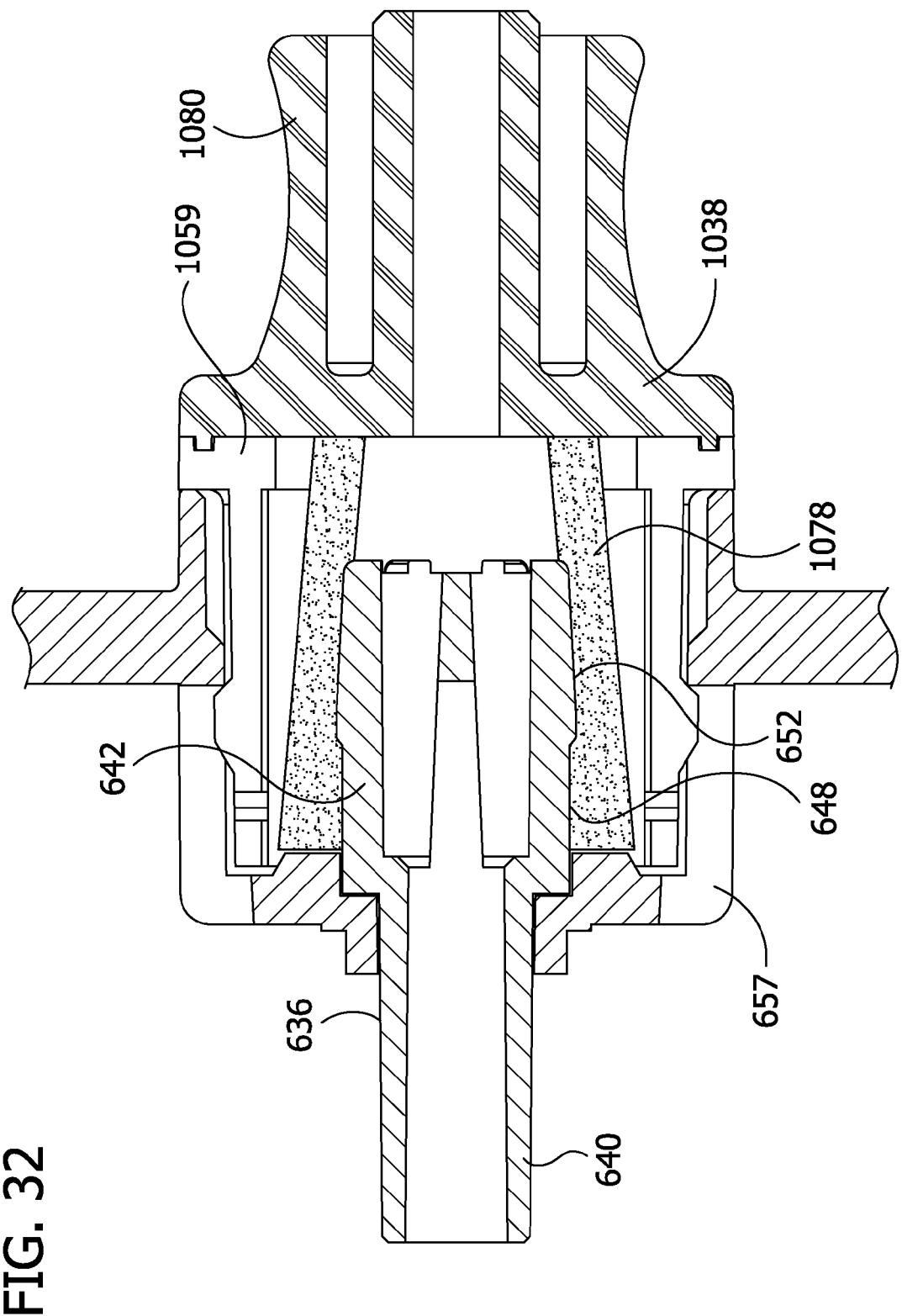
FIG. 32 is a longitudinal section through the mated first and second connectors of FIG. 31.

FIGS. 31-32 illustrate a further embodiment of the second connector 1038. Parts of the second connector 1038 corresponding to those of the connector 638 are given the same reference numerals, plus "400." The first and second housings are removed in FIG. 32 to better illustrate other features of the first and second connectors 636, 1038. The second connector 1038 differs from the second connector 938 in that the conduit 1078 of the second connector flares outward in diameter toward the free end of the second connector. This allows the outer end of the conduit 1078 to more easily receive the larger diameter non-sealing surface 652. At least one of the hardness and the thickness of the conduit 1078 is selected so that the open outer end of the conduit 1078 is capable of receiving the large diameter non-sealing surface 652 and forming a fluid-tight seal with the sealing surface 648. For example, it has been found that flared conduits 1078 with a hardness of from about 50 durometer (type A) to about 70 durometer (type A) and with a thickness of from about 30 mil to about 125 mil (about 0.762 mm to about 03.18 mm) are capable of receiving the large diameter non-sealing surface 652 and forming a fluid-tight seal with the sealing surface 648. Preferably, the inner diameter of the conduit 1078 at the open outer end is still less than the diameter of the sealing surface 648 of the first connector 636.

The second connector may form the end of a tube (e.g., the tubing 32 (FIG. 42) or the end of the second tubing 34 extending from the bladder 4 of the compression therapy device 1 (FIG. 40)) and not have a housing 1059 or attachment portion 1080 without departing from the scope of the present invention.

Figure 33:
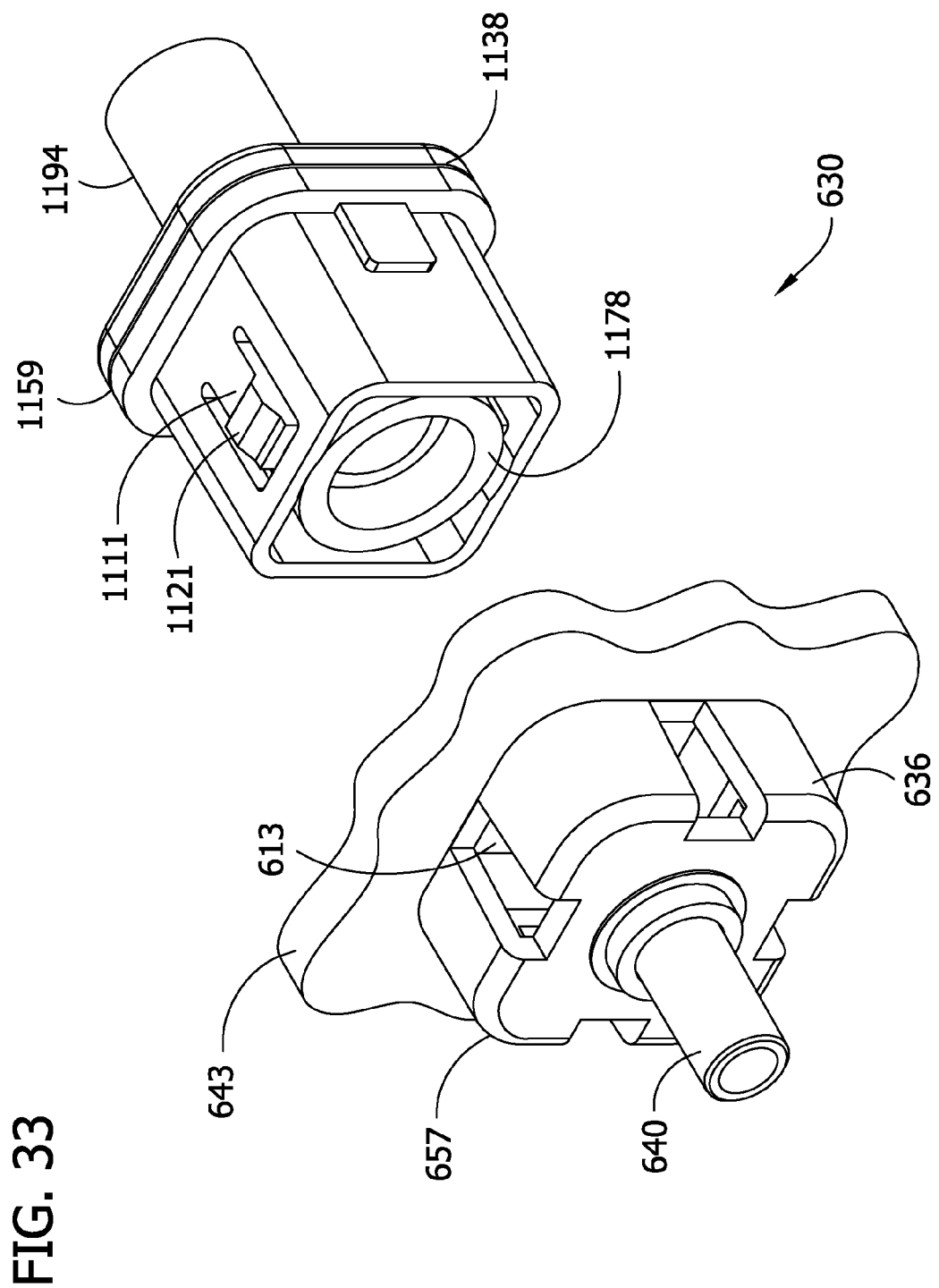
FIG. 33 is a perspective similar to FIG. 28 but showing a second connector of still another embodiment.
Figure 34:
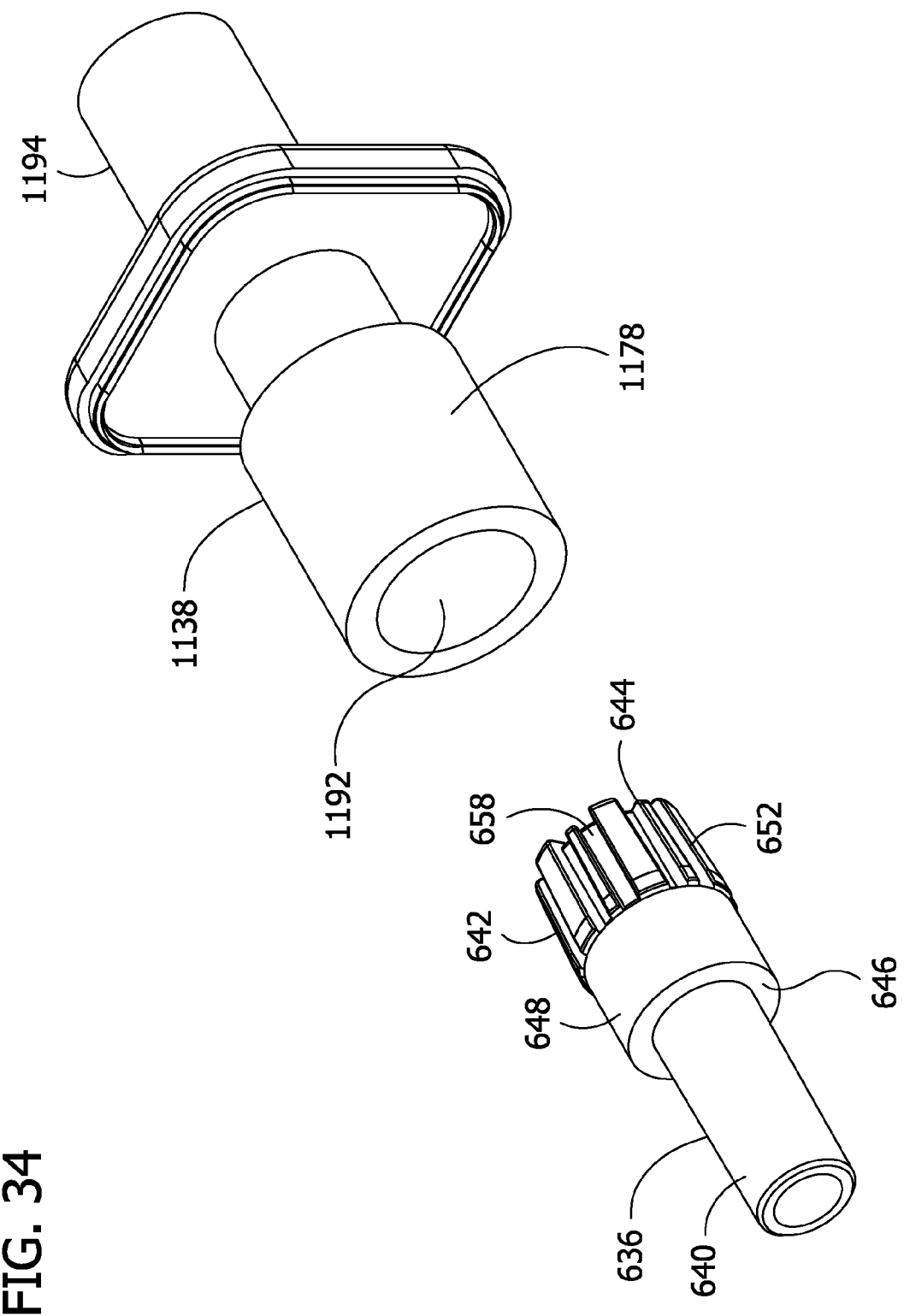
FIG. 34 is the perspective of FIG. 33 with the first and second housing removed.
Figure 35:
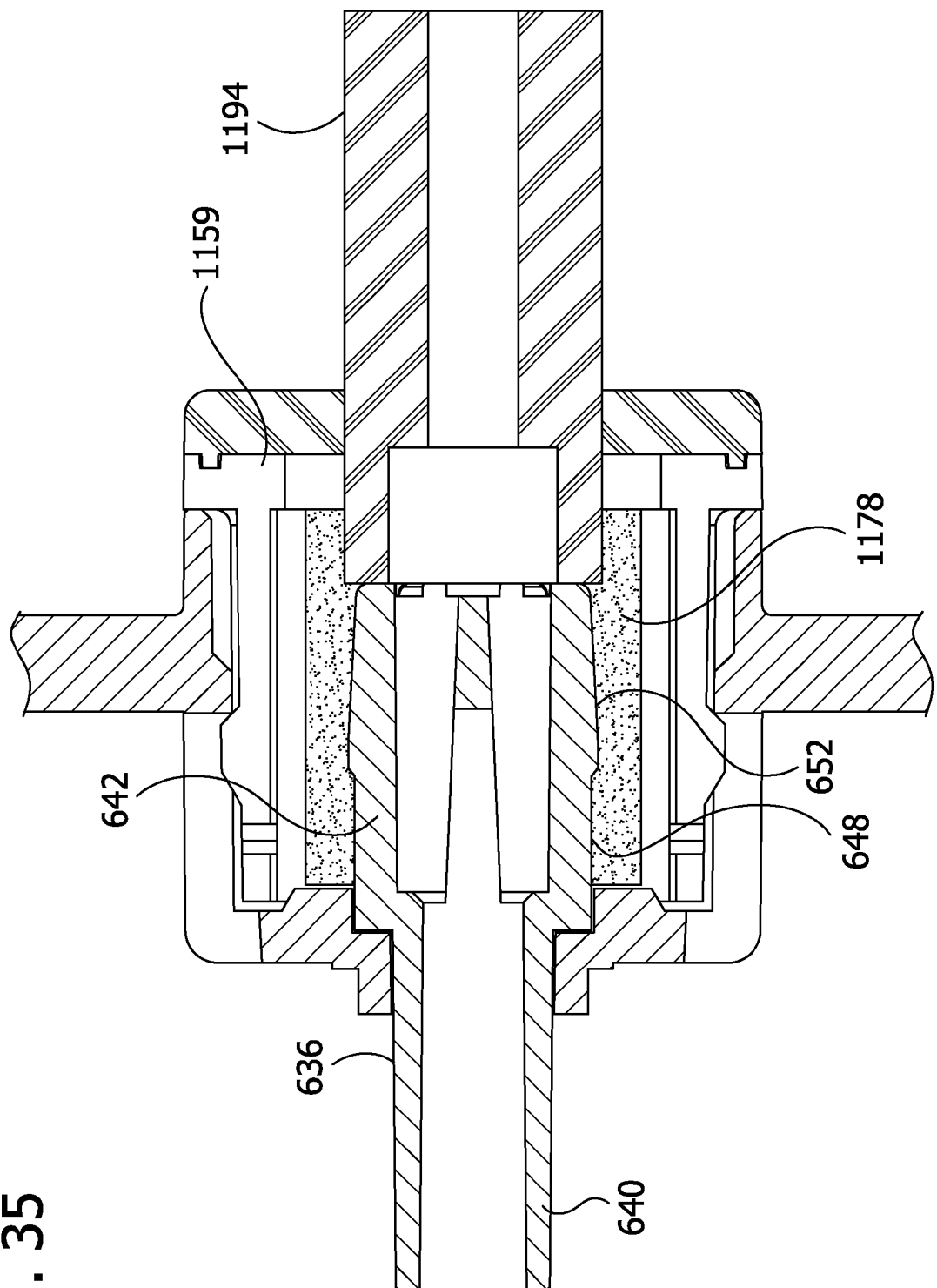
FIG. 35 is a longitudinal section of the mated connectors of FIG. 34.

FIGS. 33-35 illustrate a further embodiment of the second connector 1138. Parts of the second connector 1138 corresponding to those of the connector 638 are given the same reference numerals, plus "500." The second connector 1138 includes a second housing 1159 and conduit 1178. The first and second housings are removed in FIG. 34 to better illustrate other features of the first and second connectors 636, 1138. The conduit 1178 is connected to a first end 1192 of a tube 1194. The tube 1194 may be tubing 32 of a tube set (FIG. 42) or tubing 34 extending from the bladder 4 of the compression therapy device 1 (FIG. 40).

The first end 1192 of the tube 1194 extends into the inner end of the conduit 1178. The inside diameter of the conduit 1178 and the outside diameter of the first tube 1194 are generally the same. This allows the conduit 1178 to be suitably attached to the first end 1192 of the tube 1194, such as by solvent bending or RF welding, or the conduit 1178 may be formed as one piece of material with the tube. It will be appreciated that the flared conduit 1078 could be directly attached to a tube in the same manner (not shown).

At least one of the hardness and the thickness of the conduit 1178 is selected such that the open outer end of the conduit 1178 is capable of receiving the large diameter non-sealing surface 652 and forming a fluid-tight seal with the sealing surface 648. For example, it has been found that flared conduits 1178 with a hardness of from about 50 durometer (type A) to about 70 durometer (type A) and with a thickness of from about 30 mil to about 125 mil (about 0.762 mm to about 03.18 mm) are capable of receiving the large diameter non-sealing surface 652 and forming a fluid-tight seal with the sealing surface 648.

While the second connector 1138 is illustrated with a housing 1159, the second connector may lack a housing without departing from the scope of the present invention.

Figure 36:
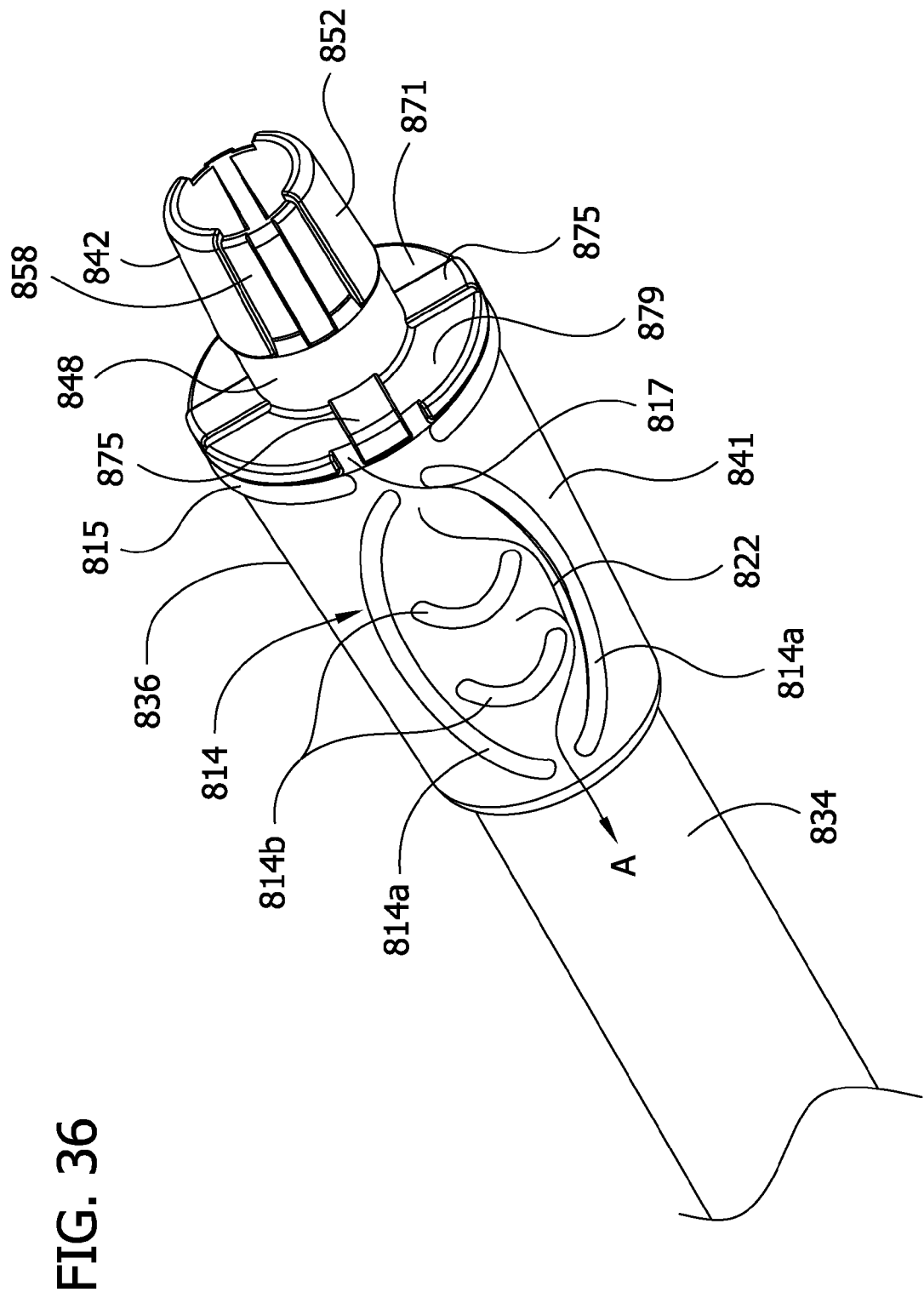
FIG. 36 is a perspective of a first connector of an alternate embodiment of the connector assembly.
Figure 37:
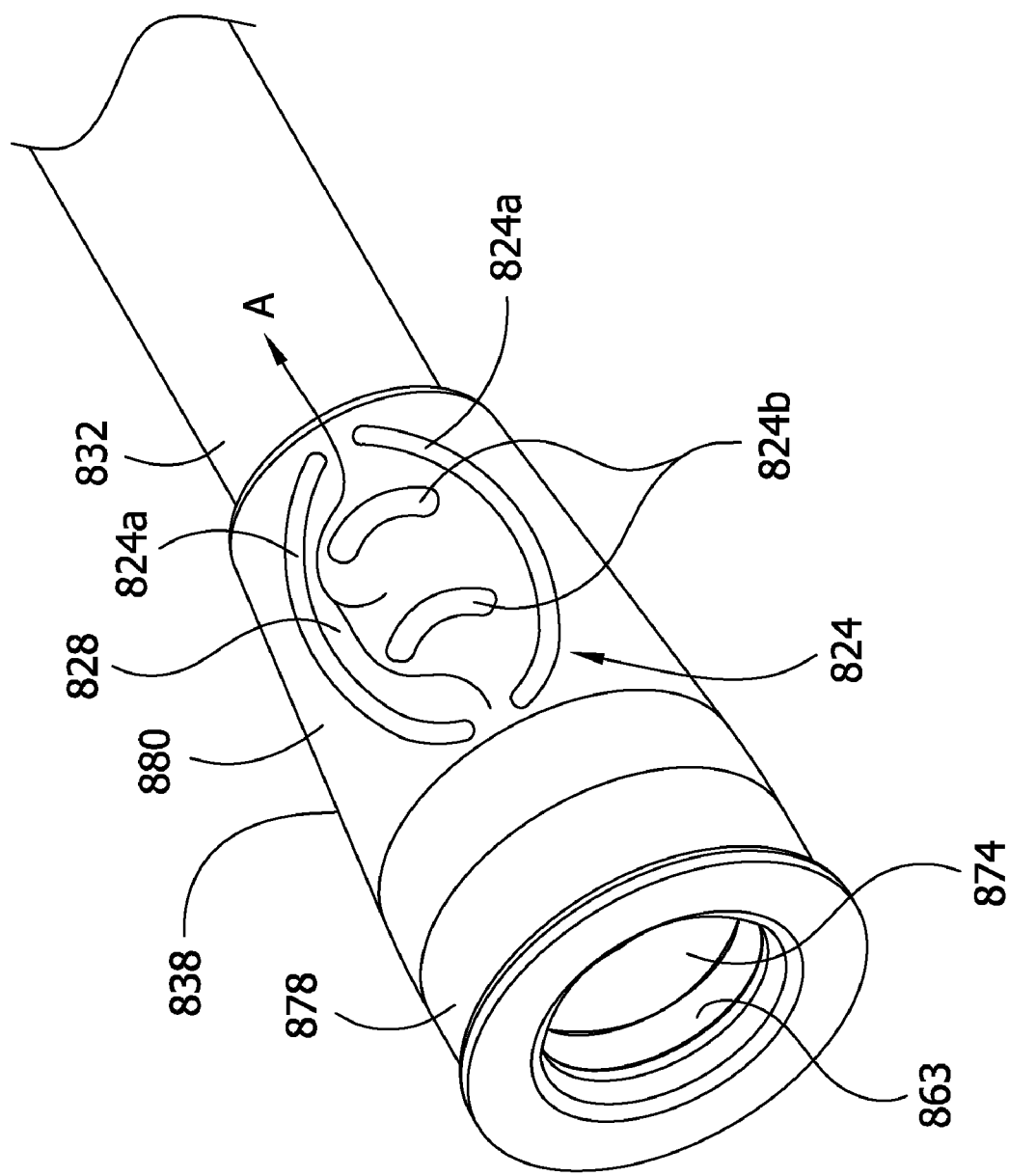
FIG. 37 is a perspective of a second connector of the connector assembly of FIG. 28 attached to tubing.
Figure 38:
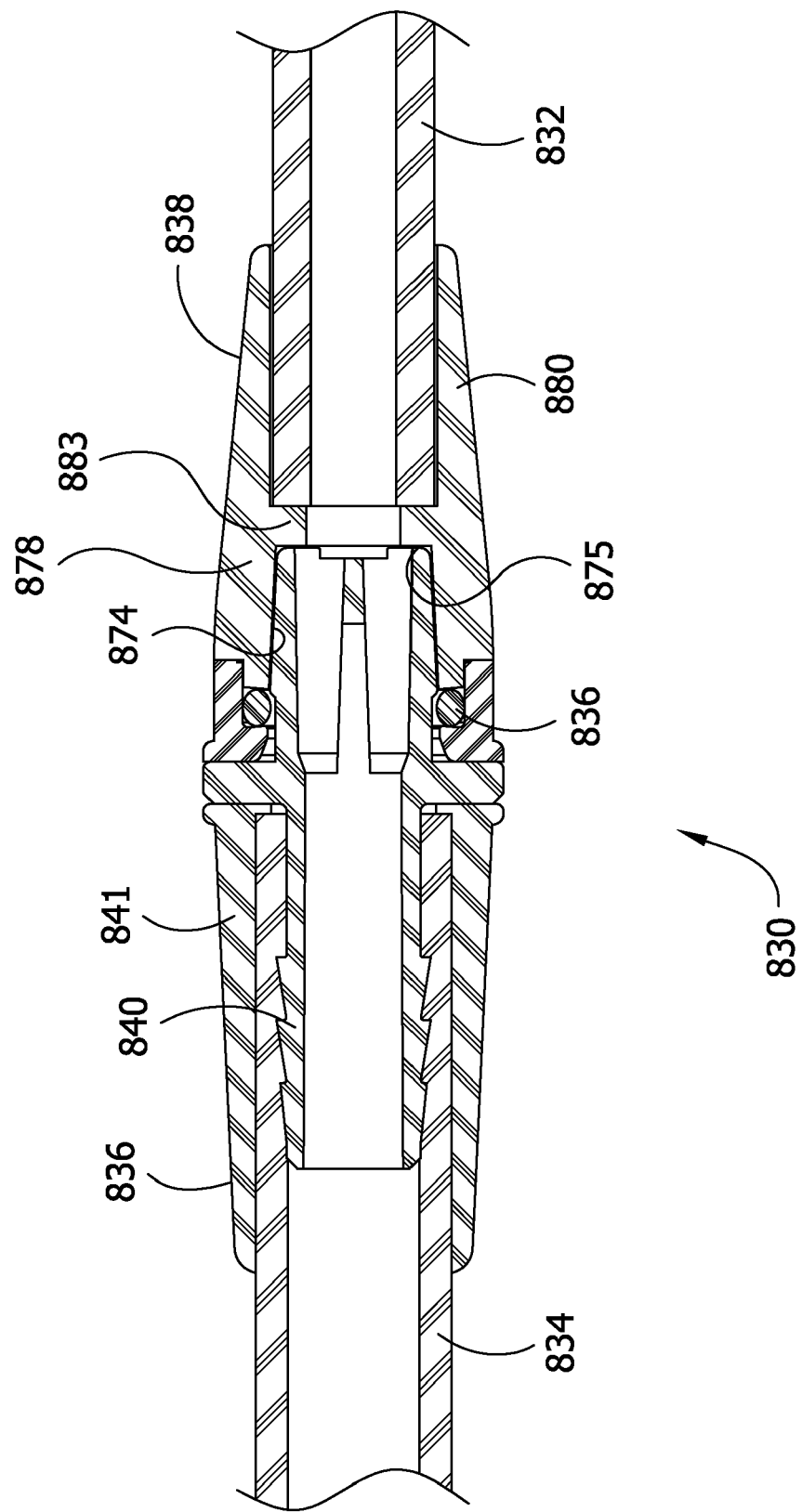
FIG. 38 is a longitudinal section of the connector assembly of FIGS. 36 and 37 with the first and second connectors of the connector assembly engaged.

FIGS. 36-39 illustrate a further embodiment of a connector assembly 830. Parts of the connector assembly 830 corresponding to those of the connector assembly 30 are given the same reference numerals, plus "800." The connector assembly 830 comprises a first connector 836 and a second connector 838 (FIGS. 36 and 37). The first connector 836 has a tubular and barbed attachment portion 840 secured to a gripping portion 841 of the first connector and located in an interior of the gripping portion (FIG. 38). The attachment portion 840 can be sealingly received in tubing 834. However, the attachment portion 840 could be directly connected to an object other than tubing, in the same way as the third connector 10 is directly connected to the controller 2. The second connector 838 has an attachment portion 880 that can attach the second connector to generic tubing 832 (e.g., like tubing 32 of the tube set 20 (FIG. 42)).

The second connector 838 includes a receptacle 878. The receptacle 878 mounts to the attachment portion 880 by way of a flange 883. The receptacle 878 has an interior surface 874 and an annular shoulder 875 at the inner end of the interior of the receptacle (FIG. 38). The shoulder 875 defines a stop surface that limits the distance the first connector 836 can be inserted into the receptacle 878 and axially positions the first connector 836 with respect to the receptacle 878.

The surface of the gripping portion 841 of the first connector 836 and the surface of the attachment portion 880 of the second connector 838 include raised ridges 814, 824. The raised ridges 814 of the first connector 836 include two generally opposed parentheses shaped first ridges 814a that extend generally lengthwise of the first connector and two flattened U-shaped second ridges 814b spaced lengthwise of the first connector and located between the first ridges (FIG. 36). Likewise, the raised ridges 824 include first ridges 824a and second ridges 824b shaped and arranged in the same way as the first ridges 814a and second ridges 814b (see, FIG. 37). In the illustrated embodiment, the first and second ridges 814a, 814b and 824a, 824b are arranged to define channels 822, 828 (respectively) for the passage of air along the connector 836, 838. The raised ridges generally indicated at 814 and 824, respectively, prevent a fluid-tight seal from forming when generic medical tubing is placed over the surface of the gripping portion 841 or of the attachment portion 880. Channels 822, 828 defined by the raised ridges 814, 824 carry fluid away from the connectors 836, 838 in a direction generally indicated by arrow "A" if such tubing (not shown) is placed over the connectors thereby inhibiting a fluid tight connection of either of the connectors 836, 838 with the medical tubing. The second ridges 814b, 824b help to prevent highly conforming tube material from sealing with and between the first ridges 814a, 824b.

It is to be understood that the ridges 814 and 824 may have shapes and arrangements that are different from what is illustrated and different from each other within the scope of the present invention. As shaped and arranged in the illustrated embodiment, the ridges 814, 824 provide for the passage of air, but also facilitate gripping the connector 836, 838. In the illustrated embodiment there are ridges (not shown) just like the ridges 814, 824 that may be seen in FIGS. 36 and 37, but which are located in the opposite sides of the connectors 836, 838.

Referring to FIG. 36, the gripping portion 841 of the first connector 836 has a flange 815 formed at a distal end. The first connector 836 includes a coupling portion 842 and a floor 871. The diameter of the floor 871 is generally the same as the diameter of the flange 815. The floor 871 and flange 815 include bleed passages 817 at their perimeters to prevent a fluid-tight seal when medical tubing is placed over the perimeters of the flange and floor. Another pair of bleed passages (not shown) like bleed passages 817 are located at the opposite side of the connector 836. It will be understood that any number of bleed passages may be employed within the scope of the present invention.

Figure 39:
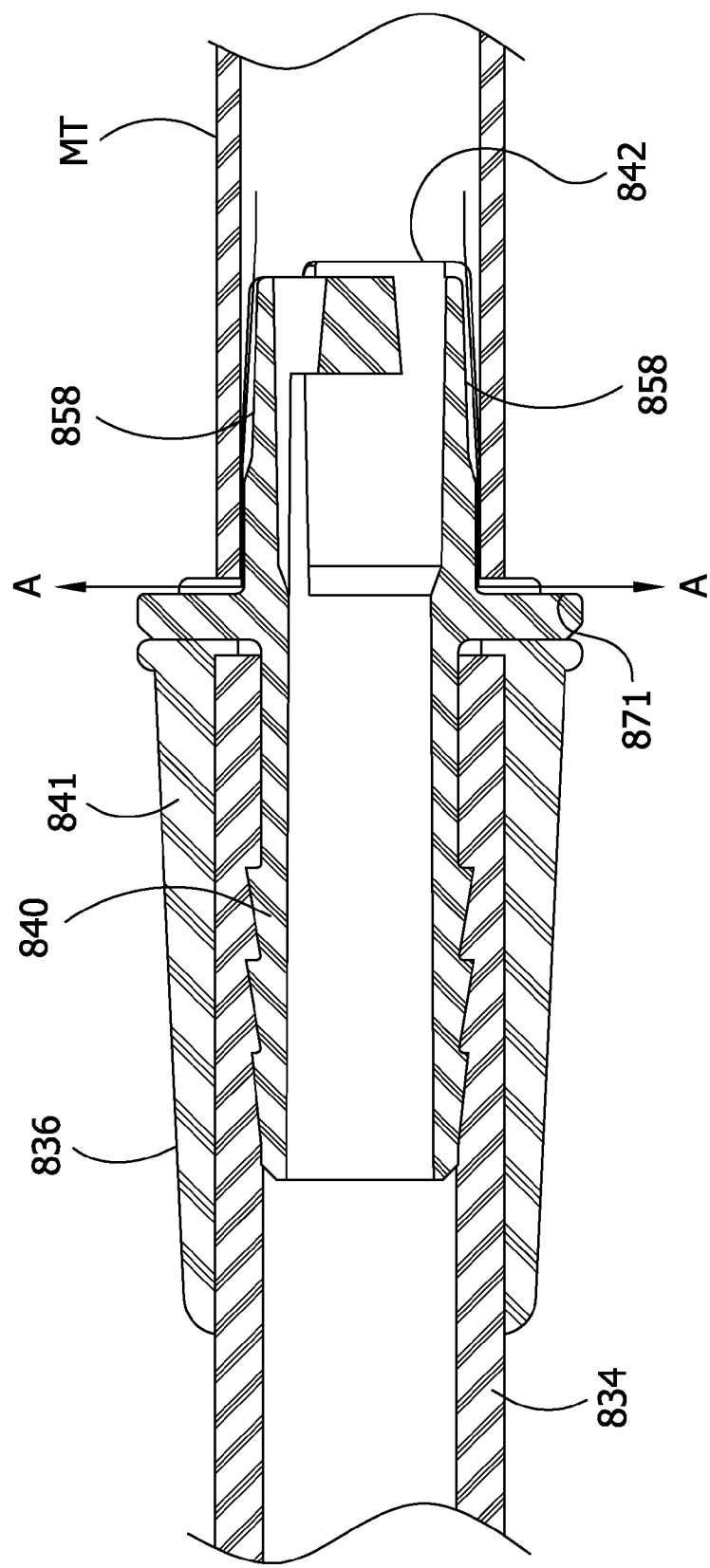
FIG. 39 is a longitudinal section taken through opposed channels of a non-sealing surface of the first connector in FIG. 36 showing attempted attachment of a non-permitted conduit.

The first connector 836 includes a coupling portion 842 that projects outward from the floor 871. Standoff ribs 875 that project outward from the floor 871 are circumferentially spaced about the coupling portion 842. Bleed passages generally indicated at 879 are defined between the ribs 875 and floor 871. The bleed passages 879 are recessed from the ribs 875 and communicate with bleed passages 817. If a medical tube MT that is too small to receive the entire connector 836 therein is pushed over the coupling portion 842 as illustrated in FIG. 39, an end of the tubing engages the ribs 875 and is held off the floor 871. Air may flow out of the tube, into the bleed passages 879 to bleed passages 817 or directed radially outward of the first connector 836. The direction and pathway of flow is generally indicated by arrow "A" (FIG. 39). The bleed passages 817, 879 prevent successful fluid-tight connection between the coupling portion 842 and medical tubing when the end face of the medical tubing is pushed all the way to the floor 871.

The coupling portion 842 includes a sealing surface 848 and a non-sealing surface 852. The non-sealing surface is closer to the free end of the first connector 836 than the sealing surface 848. The sealing surface extends around the perimeter of the coupling portion 842. The shape and contour of the coupling portion 842 is not restricted to that of the illustrated embodiment, so long as the coupling portion can engage and form a seal with the second connector 838, as will be described. The non-sealing surface 852 has a greater diameter than the sealing surface 848. A number of circumferentially spaced channels 858 in the non-sealing surface 852 extend lengthwise of the first connector 836. The channels 858 operate to inhibit the formation of a sealing connection of the coupling portion 842 with an interior surface of medical tubing.

The second connector 838 has a deformable O-ring 863 at the end of the receptacle 878 opposite the attachment portion 880. The O-ring 863 protrudes radially inward and is positioned axially so that the O-ring can sealingly engage the sealing surface 848 of the first connector 836 when the first connector 836 is received in the second connector 838 to make a fluid-tight connection. In this way, essentially only desired connections are allowed.

For the preferred embodiments described herein, the connectors are fabricated from semi-flexible and flexible materials suitable for vascular compression therapy such as, for example, polymeric materials, depending on the particular vascular therapy application and/or preference. Urethanes and silicones may also be used. One skilled in the art, however, will realize that other materials and fabrication methods suitable for assembly and manufacture, in accordance with the present disclosure, also would be appropriate. A number of alternating sealing and non-sealing surfaces is possible depending on the size and shape of the connector assembly.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above embodiments and methods without departing from the scope of the invention, it is intended that all matter contained in the above description and shown in the accompanying drawings shall be interpreted as illustrative and not in a limiting sense.

What is claimed:

1. A connector assembly for use in making discriminating fluid connection between a source of fluid and a fluid receiving object, the connector assembly comprising:
    a first connector having a coupling portion, the coupling portion including a sealing surface and a non-sealing surface, the non-sealing surface being located closer to a free end of the first connector than the sealing surface and having a larger diameter than the sealing surface;
    a second connector comprising a conduit having an open outer end, the conduit being sized to mate with the coupling portion, the conduit having at least one of a hardness and a wall thickness selected so that the conduit deforms into fluid-tight engagement with the sealing surface of the first connector while remaining in engagement with the non-sealing surface,
    the connector assembly being in combination with an inflatable vascular compression device.

2. A connector assembly as set forth in claim 1 wherein the open outer end of the conduit is sized for receiving the coupling portion of the first connector therein.

3. A connector assembly as set forth in claim 1 wherein the conduit has a hardness of from about 50 durometer (type A) to about 70 durometer (type A).

4. A connector assembly as set forth in claim 1 wherein the conduit has a wall thickness of about 30 mil to about 125 mil.

5. A connector assembly as set forth in claim 1 wherein the conduit has a hardness of from about 50 durometer (type A) to about 70 durometer (type A) and a thickness of from about 50 mil to about 100 mil.

6. A connector assembly as set forth in claim 1 wherein the second connector further comprises a housing containing the conduit.

7. A connector assembly as set forth in claim 6 wherein the housing is made of a more rigid material than the conduit and the conduit is mounted on the housing.

8. A connector assembly as set forth in claim 1 wherein the second connector is connected to and in fluid communication with an end of medical tube.

9. A connector assembly as set forth in claim 1 wherein the conduit is mounted on a medical tube having at least one of a greater hardness and a greater wall thickness than the conduit.

10. A connector assembly as set forth in claim 9 wherein the first end of the medical tube extends into an inner end of the conduit.

11. A connector assembly as set forth in claim 1 wherein an interior diameter of the conduit flares outwardly toward a free end of the conduit.

12. A compliant connector for use in making a discriminating connection with another connector having a non-sealing surface and a sealing surface where the non-sealing surface is located closer to a free end of the other connector and has a larger diameter than the sealing surface, the compliant connector comprising:
    a conduit having a hardness and wall thickness selected for simultaneously engaging the non-sealing surface and the sealing surface while deforming into fluid-tight engagement with the sealing surface; and
    a mounting structure having a greater rigidity than the conduit, wherein the mounting structure comprises a medical tube mounting the conduit thereon at a free end of the tube,
    the compliant connector being in combination with an inflatable vascular compression device.

13. A compliant connector as set forth in claim 12 wherein the medical tube has at least one of a greater hardness and a greater wall thickness than the conduit.

14. A compliant connector as set forth in claim 13 wherein the first end of the medical tube extends into an inner end of the conduit.

* * * * *